US006372225B1

(12) United States Patent
Matsuda

(10) Patent No.: US 6,372,225 B1
(45) **Date of Patent: *Apr. 16, 2002**

(54) TETANUS TOXIN FUNCTIONAL FRAGMENT ANTIGEN AND TETANUS VACCINE

(75) Inventor: Morihiro Matsuda, Suita (JP)

(73) Assignee: The Research Foundation of Microbial Diseases of Osaka University, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,880

(22) PCT Filed: Mar. 24, 1997

(86) PCT No.: PCT/JP97/00976

§ 371 Date: Sep. 24, 1997

§ 102(e) Date: Sep. 24, 1997

(87) PCT Pub. No.: WO97/35612

PCT Pub. Date: Oct. 2, 1997

(30) Foreign Application Priority Data

Mar. 23, 1996 (JP) .......................................... 8-106053

(51) Int. Cl.[7] ...................... A61K 39/02; A61K 39/00; A61K 39/08

(52) U.S. Cl. .............................. 424/236.1; 424/184.1; 424/185.1; 424/190.1; 424/234.1; 424/239.1; 424/247.1

(58) Field of Search .......................... 424/184.1, 185.1, 424/190.1, 234.1, 236.1, 239.1, 247.1

(56) References Cited

U.S. PATENT DOCUMENTS

| | | | | |
|---|---|---|---|---|
| 4,007,265 A | | 2/1977 | Helting | 424/92 |
| 4,029,765 A | | 6/1977 | Helting | 424/92 |
| 4,033,819 A | | 7/1977 | Helting | 195/29 |
| 4,200,627 A | * | 4/1980 | Helting | 424/92 |
| 4,703,005 A | | 10/1987 | Nakata et al. | 435/68 |
| 5,389,540 A | | 2/1995 | Makoff et al. | 435/69.3 |
| 5,601,826 A | | 2/1997 | Halpern | 424/190.1 |

FOREIGN PATENT DOCUMENTS

| | | |
|---|---|---|
| EP | 0209281 | 1/1987 |
| JP | 5283928 | 7/1977 |
| WO | 9015871 | 12/1990 |
| WO | 9400487 | 1/1994 |
| WO | 9403615 | 2/1994 |

OTHER PUBLICATIONS

Eisel et al. EMBO Journal 5(10): 2495–2502, 198 C.*

Fischer et al, Molecular Immunology 31(15): 1141–1148, 1994.*

Matsuda et al. Animal, Plant, and Microbial Toxins, Proc. Int. Symp., 4th (1976) Meeting Date 1974. vol. 1, 363–373.*

Mandell et al. Principles and Practices of Infectious Diseases. 4th ed. vol. 2, Churchill Livingstone Inc. 1995 p. 2781 Immunization Practices Advisory Committee. Clin Pharm 8:839–850 1989.*

Vaccine 2nd ed., edited by S. A. Plotokin and E. A. Mortimer, pp. 75–77, W. B. Saunders Company.

"Mandell, Douglas and Bennett's Principles and Practices of Infectious Diseases", 4th ed., edited by G. L. Mandell et al., p. 2781, Churchhill Livingstone & Son, Inc., 1995.

Journal of American Medical Association, 247(1), pp. 40–42, 1982.

Journal of American Medical Association, 264(18), p. 2448, 1990.

Journal of American Medical Association, 271(20), p. 1629, 1994.

The Lancet, 339, pp. 1111–1112, May 2, 1992.

EMBO J., 5(10), 2495–2502, 1986.

Nucleic Acid Res., 14(19), 7809–7812, 1986.

Infection and Immunity, 57(11), 3498–3505, 1989.

Mol. Immunol., 31(15), 1141–1148, 1994.

* cited by examiner

*Primary Examiner*—Rodney P Swartz
(74) *Attorney, Agent, or Firm*—Birch, Stewart, Kolasch & Birch, LLP

(57) ABSTRACT

Disclosed is a tetanus toxin functional fragment antigen (FFA), comprising at least one fragment which is substantially the same as that obtained by a process comprising the steps of splitting at least one peptide bond selected from peptide bonds individually connecting mutually adjacent amino acid residues in a partial amino acid sequence between two cysteine residues participating in forming a disulfide bridge present in the N-terminal of the entire amino acid sequence of the whole tetanus toxin molecule, splitting the disulfide bridge, and splitting non-covalent bonds between groups on the tetanus toxin molecule; wherein the tetanus toxin FFA has a molecular weight of from 90,000 to 110,000 as measured by an SDS-polyacrylamide gel electrophoresis method, and an isoelectric point of 7.25±0.5 as measured by an isoelectric focusing method. The FFA of the present invention not only has a satisfactory immunopotency as a tetanus vaccine antigen, that is, has an immunopotency which is substantially the same as that of a whole tetanus toxin toxoid, but is also extremely excellent with respect to the diminution of adverse side effects. Further, the present invention provides a method for mass production of the FFA, and a tetanus vaccine comprising the FFA, and a combined vaccine comprising the tetanus vaccine and at least one vaccine other than the tetanus vaccine.

4 Claims, 2 Drawing Sheets

TETANUS TOXIN FUNCTIONAL FRAGMENT ANTIGEN AND TETANUS VACCINE

BACKGROUND OF THE INVENTION

1. Technical Field

The present invention relates to a tetanus toxin functional fragment antigen and a tetanus vaccine comprising the same. More particularly, the present invention is concerned with a specific tetanus toxin functional fragment antigen which is extremely useful as an antigen for a tetanus vaccine since the functional fragment antigen is advantageous not only in that it is extremely excellent with respect to the diminution of side effects when used as an antigen, as compared to the current tetanus vaccine comprising as an antigen a whole tetanus toxin toxoid, but also in that it has an immunopotency which is substantially the same as that of the whole tetanus toxin toxoid. The present invention is also concerned with a very safe and effective tetanus vaccine (tetanus toxoid) comprising the tetanus toxin functional fragment antigen as an active component, a combined vaccine comprising the tetanus vaccine and at least one vaccine other than the tetanus vaccine, and methods for producing the fragment antigen and vaccines.

2. Prior Art

As is well known, tetanus is an infectious disease with extremely high mortality which produces serious symptoms, such as opisthotonos and dyspnea. Tetanus bacilli are widely distributed in the environments, and their spores are commonly found in soil, feces of animals, and the like. Therefore, every individual is exposed to the danger of tetanus infection from various types of traumas, such as punctured wounds and crushed wounds. Moreover, when an individual is infected with tetanus bacilli, conventional chemotherapies using antibiotics, muscle relaxants and the like cannot grossly change the mortality, whether tetanus patients are elderly or young. In developed countries, most deaths from tetanus have recently occurred among the elderly patients who escaped from vaccination against tetanus in their babyhood.

Further, even when an individual receives tetanus vaccination in baby- or child-hood for basal immunization and receives a booster, the immunity remaining in adulthood is not sufficient for preventing tetanus infection when the individual suffers unexpected injury in earthquakes, fires, traffic accidents or the like. Therefore, it is important for adults of the ages above ca. 40, especially elderly persons, to receive personally a booster injection in order to ensure protection against tetanus.

In developed countries, an increase in the number of intrahospital childbirths, and improvements in living environments and sanitation, an improvement in the quality of emergency medical care with respect to the provision of toxoids and antitoxins, and compulsory vaccinations for younger people, have reduced the number of tetanus patients to 1/30 of that of half a century ago. Furthermore, tetanus is a non-epidemic disease and is not transmitted from person to person. Therefore, the importance of the prevention of this disease tends to be overlooked. However, even today, the number of tetanus deaths in the world is estimated to be about 1 million per year, including mostly neonatal tetanus deaths which are prevailing in developing countries. In addition, due to widespread drug abuse, the number of tetanus patients infected through contaminated injection needles is also increasing recently.

Under these circumstances, tetanus is now recognized as a disease to be prevented by vaccination, rather than to be treated, and preventive measures against tetanus are being actively undertaken. For example, in the Expanded Program of Immunization (EPI) of the World Health Organization (WHO), vaccination against tetanus is being adopted as one of the most important tasks, and the vaccination program is being promoted. The "International Conference on Tetanus", one of whose goals is to eradicate the tetanus disease has been held about every three years in various countries since 1963.

As evident from the above, tetanus is a disease caused by a ubiquitous bacteria whose spores are impossible to eradicate from the earth, and it is not an exaggeration to say that vaccination against tetanus is the only way to reduce the death of human beings due to tetanus, irrespective of age and sex, to zero, and that the vaccination is essential for all human beings who are born on the earth not only at present, but also in the future.

For prevention of tetanus, tetanus toxoid has been used as a vaccine. Tetanus toxoid, which is used as an active component for tetanus vaccine, is tetanus toxin detoxified with formalin. Such a tetanus toxoid has been used in either a plain form without an adjuvant or in the form of a precipitated antigen preparation adsorbed on a small amount of an aluminum salt as an adjuvant or in the form of a combined antigen preparation prepared by mixing tetanus toxoid with other vaccines, such as diphtheria toxoid, pertussis vaccine and Haemophilus influenzae b vaccine. To infants, tetanus toxoid is generally administered in the form of the so-called DPT combined vaccine which is a mixture of vaccines of diphtheria (D), tetanus (T) and pertussis (P) in adsorbed forms. For a tetanus-prophylactic treatment of traumatic patients, a plain T toxoid vaccine or a DT combined toxoid vaccine is used. These toxoids are widely used over the world and the T toxoid preparations have been highly appreciated in the world as one of the most effective and important vaccines. However, the current tetanus toxoid preparations have various problems to be solved. For example, the tetanus toxoid has disadvantages in that there are various adverse side effects, that the product quality is uneven among different manufacturers, that the retention of immunity is limited to only approximately 5 to 10 years and, therefore, repeated vaccinations are necessary to keep the antitoxin level sufficient to prevent tetanus infection. Thus, the conventional tetanus toxoid has problems to be solved with respect to safety, control of quality, retention of immunity, and ease, labor saving and economy in administration. Therefore, for promoting the use of the tetanus vaccine, a large number of problems need to be solved mainly from a viewpoint of mass-production of high quality tetanus vaccine.

Hereinbelow, prior art is discussed in connection with the primary object of the present invention, which is to provide a tetanus toxin antigen, which is not only extremely excellent with respect to the diminution of adverse side effects when used as a vaccine, but also exhibits high immunopotency, thus solving the above-mentioned problems accompanying the prior art.

Various adverse side effects are known to accompany the use of conventional tetanus toxoid vaccines. Various adverse side effects, such as local reactions at injection sites (e.g., erythema, tenderness, swelling, edema and sterile abscess), systemic fever; and, although rare, allergy (e.g., local anaphylaxis, anaphylactic shock, serum sickness-like type III hypersensitivity and delayed hypersensitivity) and serious generalized reactions (e.g., peripheral neuropathy, lymphadenopathy, brachial plexus neuropathy, Guillain-Barret syndrome and acute transverse myelitis) have been reported (see “Vaccine”, 2nd edition, edited by S. A. Plotkin and E. A. Mortimer, pp. 75–77, W. B. Saunders Company, 1994; “Mandell, Douglas and Bennett’s Principles and Practice of Infectious Diseases”, 4th edition, edited by G. L. Mandell et al., p. 2781, Churchill Livingstone & Son, Inc., 1995; Journal of the American Medical Association, 264 (18), p. 2448, 1990 and 271(20), p. 1629, 1994; and Lancet, 339, pp. 1111–1112, May 2, 1992).

Various attempts to reduce or remove these adverse side effects of the tetanus toxoid vaccine have been made. For example, development of a method for obtaining highly purified toxoid, use of modified or new adjuvants, and individual use of the fragments A, B and C (which are subunits of the tetanus toxin and which are explained below) as an active component for a vaccine have been proposed. Of these attempts, with respect to the techniques of using a tetanus toxin fragment, as examples of tetanus toxin fragments used in these techniques, there can be mentioned fragment A or C prepared by digesting the tetanus toxin with trypsin and/or papain (see Unexamined Japanese Patent Application Laid-Open Specification Nos. 50-71820, 51-82719 and 52-83928), fragment A-B prepared by digesting the tetanus toxin with papain (see Unexamined Japanese Patent Application Laid-Open Specification No. 53-26319), an antigen obtained by expressing a gene coding for fragment C in *E. coli*, yeast or salmonella (see Unexamined Japanese Patent Application Laid-Open Specification No. 3-285681, Japanese Patent Application prior-to-examination Publication (Kohyo) No. 4-506005, corresponding to International Application Publication No. WO 90/15871, International Application Publication No. WO 94/03615, and EP-A-0 209 281), and a synthesized epitope of fragment C (see International Application Publication No. WO 94/00484). However, none of these conventional tetanus toxin fragment vaccines have been put into practical use because all of these tetanus toxin fragment vaccines have low antigenicity and immunopotency, as compared to those of the conventional tetanus toxoid comprising the toxoid of the whole tetanus toxin molecule. Meanwhile, cloning of the tetanus toxin gene, and determination of both nucleotide sequence and amino acid sequence of the tetanus toxin molecule have been achieved [see EMBO Journal, 5(10), 2495–2501, 1986 and Nucleic Acid Research, 14(19), 7809–7812, 1986 (the entire amino acid sequence of the whole tetanus toxin molecule is shown in SEQ ID NO. 1)]. Further, based on the above information on the entire nucleotide sequence and amino acid sequence, fragments of the tetanus toxin gene are expressed and synthetic peptides are produced as parts of the tetanus toxin molecule, and in addition, determination of the epitope regions of the tetanus toxin has been attempted using the expression products of the gene DNA fragments and the synthesized peptides [see Infection and Immunity, 57(11), 3498–3505, 1989 and Molecular Immunology, 31(15), 1141–1148, 1994]. However, tetanus vaccines comprising such tetanus toxin epitopes as active components have not been achieved.

SUMMARY OF THE INVENTION

The present inventor has long studied tetanus toxin to date for more than 20 years since the early 1970s, when purification of tetanus toxin to a high level could not be achieved and the detailed structure and properties of the tetanus toxin molecule were unknown. The present inventor extensively studied the toxin-producing ability of tetanus bacilli. He has further made extensive and intensive studies for developing a tetanus vaccine antigen which is extremely excellent with respect to diminution of adverse side effects of conventional tetanus vaccines comprising, as an antigen, the whole tetanus toxin toxoid, but also has an immunopotency which is substantially the same as that of the whole tetanus toxin toxoid. As a result, he found that a specific functional fragment antigen (hereinafter referred to simply as “FFA”) derived from tetanus toxin is effective as an antigen for a tetanus vaccine, and is extremely excellent with respect to diminution of adverse side effects. The present invention has been completed, based on the novel findings.

Therefore, it is an object of the present invention to provide a tetanus antigen which is extremely excellent with respect to diminution of adverse side effects of the conventional whole tetanus toxin toxoid, but also has an immunopotency which is substantially the same as that of a whole tetanus toxin toxoid.

It is another object of the present invention to provide a tetanus vaccine which is extremely excellent with respect to the diminution of adverse side effects of the current vaccines, and has an immunopotency which is substantially the same as that of the conventional whole tetanus toxoid vaccine.

A further object of the present invention is to provide a method for producing the above-mentioned tetanus vaccine.

Still a further object of the present invention is to provide a method for producing the above-mentioned functional fragment antigen (FFA) as a tetanus vaccine antigen.

The foregoing and other objects, features and advantages of the present invention will be apparent to those skilled in the art from the following detailed description and appended claims taken in connection with the accompanying sequence listing and drawings.

BRIEF DESCRIPTION OF THE SEQUENCE LISTING

SEQ ID NO. 1 is one form of the entire amino acid sequence of the whole tetanus toxin molecule used in the present invention.

BRIEF DESCRIPTION OF THE DRAWINGS

In the accompanying drawings:

FIG. 1(*b*) is a diagrammatic view of a nicked form of the whole tetanus toxin molecule;

FIG. 1(*c*) shows a tripartite [A-B·C] model of the whole tetanus toxin molecule;

FIG. 2(*b*) is a diagrammatic view of a structural model of the whole tetanus toxin molecule.

DESCRIPTION OF REFERENCE CHARACTERS

S - - - S: disulfide bridge

*: nick

- - - : non-covalent bond

In the one-letter representation system for representing the amino acid residues of an amino acid sequence, the letters respectively represent the following amino acid residues:

| | | | | | |
|---|---|---|---|---|---|
| A | Alanine | C | Cysteine | D | Aspartic acid |
| E | Glutamic acid | F | Phenylalanine | G | Glycine |
| H | Histidine | I | Isoleucine | K | Lysine |
| L | Leucine | M | Methionine | N | Asparagine |
| P | Proline | Q | Glutamine | R | Arginine |
| S | Serine | T | Threonine | V | Valine |
| W | Tryptophan | Y | Tyrosine. | | |

DETAILED DESCRIPTION OF THE INVENTION

Figure 2A:
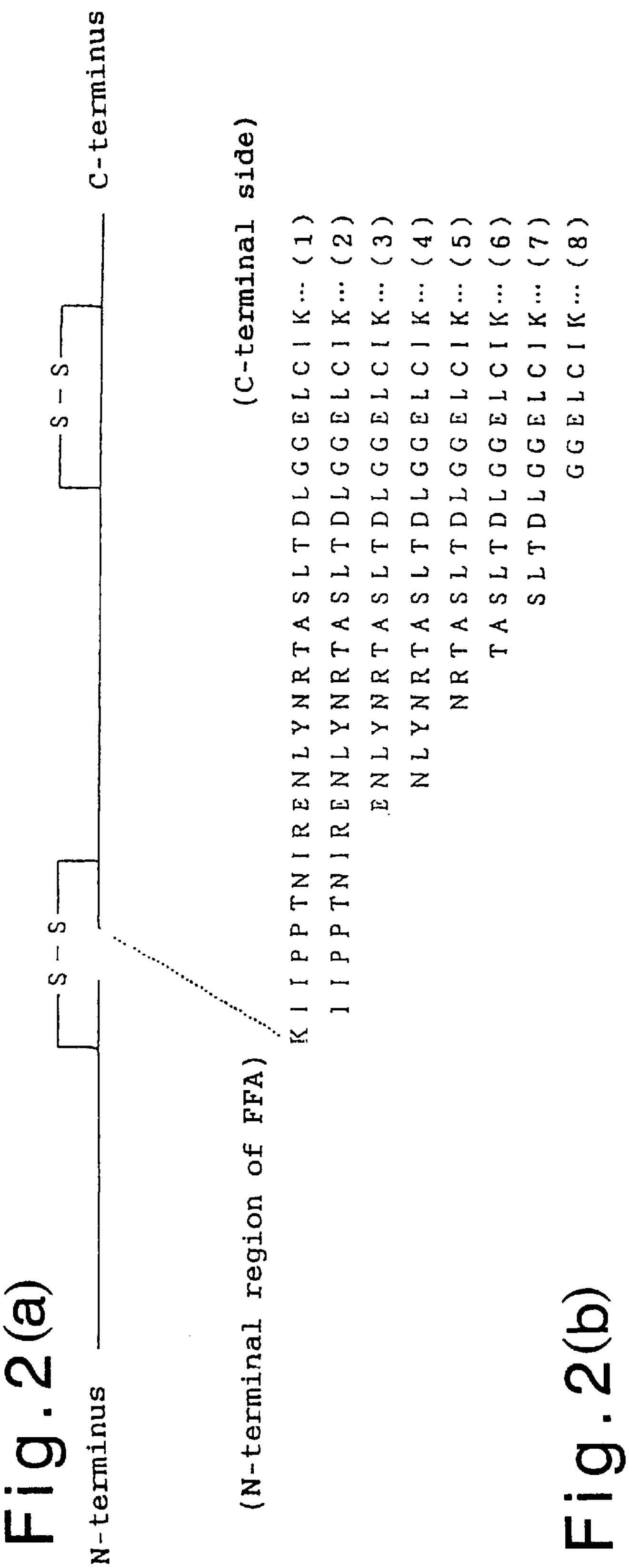
FIG. 2(*a*) is a diagrammatic view showing a variety of the N-terminal amino acid sequences of the tetanus toxin functional fragment antigen (SEQ ID NO: 2–9.
Figure 2B:
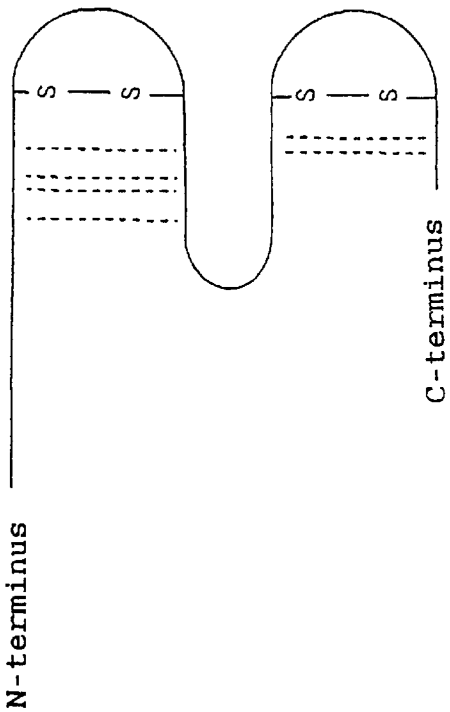

According to the present invention, there is provided a tetanus toxin functional fragment antigen, comprising at least one fragment which is substantially the same as that obtained by a process comprising the steps of splitting at least one peptide bond selected from peptide bonds individually connecting mutually adjacent amino acid residues in a partial amino acid sequence between two cysteine residues participating in forming a disulfide bridge present in the N-terminal of the entire amino acid sequence of a whole tetanus toxin molecule, splitting the disulfide bridge, and splitting non-covalent bonds [as indicated in FIG. 2(*b*)] between groups on the tetanus toxin molecule;

the tetanus toxin functional fragment antigen having:

(a) a molecular weight of from 90,000 to 110,000 as measured by an SDS-polyacrylamide gel electrophoresis method; and (b) an isoelectric point of 7.25±0.5 as measured by an isoelectric focusing method.

For easy understanding of the present invention, the essential features and various preferred embodiments of the present invention are enumerated below.

1. A tetanus toxin functional fragment antigen, comprising at least one fragment which is substantially the same as that obtained by a process comprising the steps of splitting at least one peptide bond selected from peptide bonds individually connecting mutually adjacent amino acid residues in a partial amino acid sequence between two cysteine residues participating in forming a disulfide bridge present in the N-terminal of the entire amino acid sequence of a whole tetanus toxin molecule, splitting the disulfide bridge, and splitting non-covalent bonds between groups on the tetanus toxin molecule;

the tetanus toxin functional fragment antigen having:

(a) a molecular weight of from 90,000 to 110,000 as measured by an SDS-polyacrylamide gel electrophoresis method; and (b) an isoelectric point of 7.25±0.5 as measured by an isoelectric focusing method.

2. The tetanus toxin functional fragment antigen according to item 1 above, wherein each of the at least one fragment independently has an amino acid sequence selected from the group consisting of SEQ ID NOS:10–17. The N-terminal amino acid sequence of each of SEQ ID NOS:10–17 is represented by SEQ ID NOS:2–9, respectively. SEQ ID NOS:2–9 are depicted below as amino acid sequences (1) to (8), respectively.

(1) KIIPPTNIRENLYNRTASLTDLGGELCIK (SEQ ID NO:2), (2) IIPPTNIRENLYNRTASLTDLGGELCIK (SEQ ID NO:3), (3) ENLYNRTASLTDLGGELCIK (SEQ ID NO:4), (4) NLYNRTASLTDLGGELCIK (SEQ ID NO:5), (5) NRTASLTDLGGELCIK (SEQ ID NO:6), (6) TASLTDLGGELCIK (SEQ ID NO:7), (7) SLTDLGGELCIK (SEQ ID NO:8), and (8) GGELCIK (SEQ ID NO:9). has an amino acid sequence selected from the group consisting of SEQ ID NOS:2–9. The N-terminal amino acid sequence of each of SEQ ID NOS: 2–9 is depicted below as amino acid sequences (1) to (8), respectively.

3. The tetanus toxin functional fragment antigen according to item 1 or 2 above, which is stabilized with a fixative.

4. A tetanus vaccine comprising, as an active component, the tetanus toxin functional fragment antigen of any one of items 1 to 3 above in an effective immunogenic amount.

5. A combined vaccine comprising, as one of a plurality of active components, the tetanus toxin functional fragment antigen of any one of items 1 to 3 above in an effective immunogenic amount.

6. A method for producing a tetanus vaccine, which comprises stabilizing a tetanus toxin functional fragment antigen with a fixative, the tetanus toxin functional fragment antigen comprising at least one fragment which is substantially the same as that obtained by a process comprising the steps of collecting and purifying an extracellular tetanus toxin from a culture filtrate of *Clostridium tetani* to obtain an extracellular tetanus toxin molecule, splitting a disulfide bridge present in the N-terminal of the entire amino acid sequence of the extracellular tetanus toxin molecule, and splitting non-covalent bonds between groups on the extracellular tetanus toxin molecule;

the tetanus toxin functional fragment antigen having:

(a) a molecular weight of from 90,000 to 110,000 as measured by an SDS-polyacrylamide gel electrophoresis method; and (b) an isoelectric point of 7.25±0.5 as measured by an isoelectric focusing method.

7. A method for producing a tetanus toxin functional fragment antigen, comprising:

ligating a DNA coding for the tetanus toxin functional fragment antigen of item 1 or 2 above to a vector;

transforming host cells, exclusive of *Clostridium tetani*, with the vector; and expressing the DNA coding for the tetanus toxin functional fragment antigen.

Hereinbelow, the present invention is described in detail.

In the present invention, Ala represents an alanine residue, Arg represents an arginine residue, Asn represents an asparagine residue, Asp represents an aspartic acid residue, Cys represents a cysteine residue, Gln represents a glutamine residue, Glu represents a glutamic acid residue, Gly represents a glycine residue, His represents a histidine residue, Ile represents an isoleucine residue, Leu represents a leucine residue, Lys represents a lysine residue, Met represents a methionine residue, Phe represents a phenylalanine residue, Pro represents a proline residue, Ser represents a serine residue, Thr represents a threonine residue, Trp represents a tryptophan residue, Tyr represents a tyrosine residue and Val represents a valine residue.

As mentioned above, the tetanus toxin functional fragment antigen of the present invention comprises at least one fragment which is substantially the same as that obtained by a process comprising the steps of splitting at least one peptide bond selected from peptide bonds individually connecting mutually adjacent amino acid residues in a partial amino acid sequence between two cysteine residues participating in forming a disulfide bridge present in the N-terminal of the entire amino acid sequence of a whole tetanus toxin molecule, splitting the disulfide bridge, and splitting non-covalent bonds [as indicated in FIG. 2(*b*)] between groups on the tetanus toxin molecule.

As a preferred embodiment of the tetanus toxin functional fragment antigen of the present invention, there can be mentioned the tetanus toxin functional fragment antigen, wherein each of the above-mentioned at least one fragment independently has an amino acid sequence selected from the group consisting of SEQ ID NOS:10–17. The N-terminal amino acid sequence of each of SEQ ID NOS:10–17 is represented by SEQ ID NOS:2–9, respectively. SEQ ID NOS:2–9 are depicted below as amino acid sequences (1) to (8), respectively.

(1) KIIPPTNIRENLYNRTASLTDLGGELCIK (SEQ ID NO:2), (2) IIPPTNIRENLYNRTASLTDLGGELCIK (SEQ ID NO:3), (3) ENLYNRTASLTDLGGELCIK (SEQ ID NO:4), (4) NLYNRTASLTDLCGELCIK (SEQ ID NO:5), (5) NRTASLTDLGGELCIK (SEQ ID NO:6), (6) TASLTDLGGELCIK (SEQ ID NO:7), (7) SLTDLGGELCIK (SEQ ID NO:8), and (8) GGELCIK (SEQ ID NO:9).

Further, the tetanus toxin functional fragment antigen of the present invention may be stabilized with a fixative.

For further clarification of the essential features of the present invention, the technical features of the present invention will be described by explaining the development of the present invention.

Isolation of a Strain of *Clostridium tetani* having High Toxin-producing Ability:

In the present invention, a strain of *Clostridium tetani* having high toxin-producing ability is used. The present inventor isolated a substrain having high toxin-producing ability by single colony isolation from Harvard H47 strain, which is a known *C. tetani* strain derived from a known *C. tetani* strain called the Harvard strain [ATCC (American Type Culture Collection) accession No. 10779], and he designated the obtained substrain as "*Clostridium tetani* Harvard H47 strain Biken substrain" (hereinafter referred to simply as "Biken substrain"). Also, the present inventor found that production of tetanus toxin is under the control of genetic information carried by the plasmid DNA in the *C. tetani* cell (Biken Journal, 20, 105–115, 1977). Further, by using the culturing method based on the above finding, the present inventor succeeded in mass production of tetanus toxin by culturing the Biken substrain, and high purification of the tetanus toxin.

Thus, in the present invention, it is first necessary that a strain of *Clostridium tetani* having high toxin-producing ability is selected and used as a seed culture. As a seed culture, a culture of transformant of a microorganism, such as yeast, *Escherichia coli, Bacillus subtilis* or the like, which is obtained using the below-mentioned DNA coding for FFA, by genetic engineering techniques, can be used.

Mode of Formation of and Toxic Activity of Tetanus Toxin:

In the *C. tetani* cells, tetanus toxin is first produced in the form of a single polypeptide chain (whole tetanus toxin molecule in a non-nicked, intact form) having a molecular weight of about 150,000 (hereinafter, frequently referred to as "intracellular toxin"). Subsequently, by the autolysis of the cell, the tetanus toxin is released from the cells into the extracellular medium (hereinafter, the toxin released into the extracellular medium is frequently referred to as "extracellular toxin"). When the toxin is released from the cells, at least one bond in the peptide bonds connecting mutually adjacent amino acid residues in the partial amino acid sequence between two cysteine residues participating in forming the disulfide bridge present in the N-terminal of the whole amino acid sequence of the whole tetanus toxin molecule is split by a protease produced by *C. tetani*, to thereby form at least two polypeptide chains. However, the two polypeptide chains are united to each other by the disulfide bridge present in the N-terminal of the whole tetanus toxin molecule, that is, these polypeptide chains assume a nicked forms [see FIGS. 1(*a*) and 1(*b*); Biochemical and Biophysical Research Communications, 57, 1257–1262, 1974; ibid. 68, 668–674, 1976; ibid. 77, 268–274, 1977], and further, the two polypeptide chains are also united to each other by non-covalent bonds [see FIG. 2(*b*)]. Conversion of the tetanus toxin molecule from the intact form into the nicked form enhances the toxin activity of the tetanus toxin several times, and the nicking is essential for eliciting toxic action. Therefore, for saving labor in the preparation of the functional fragment antigen, it is preferred to use, as a starting material, the extracellular tetanus toxin, which has already been converted into the nicked form [see FIG. 1(*b*)].

Subunit Structure of Tetanus Toxin and the Mechanism of Manifestation of Toxicity of Tetanus Toxin:

As a result of the unique studies of the present inventor, two functionary complementary polypeptide chains, namely, L (light) chain and H (heavy) chain, were obtained from the whole tetanus toxin molecule. That is, the present inventor succeeded in isolating and purifying these fragments (L and H chains), to thereby obtain the L chain and H chain individually, which are native enough to be able to reproduce the toxin activity of the whole tetanus toxin molecule when these L and H chains are reconstituted into the whole tetanus toxin molecule, although each of the individually obtained L chain and H chain is not toxic.

In addition, the present inventor also successfully isolated and purified the following three fragments: the C-terminal half of the H chain (fragment C), a fragment (fragment A-B) obtained by removing fragment C from the whole tetanus toxin molecule, and a fragment (fragment B) obtained by separating fragment A (i.e., L chain) from the purified fragment A-B.

Figures 1A, 1B, 1C:
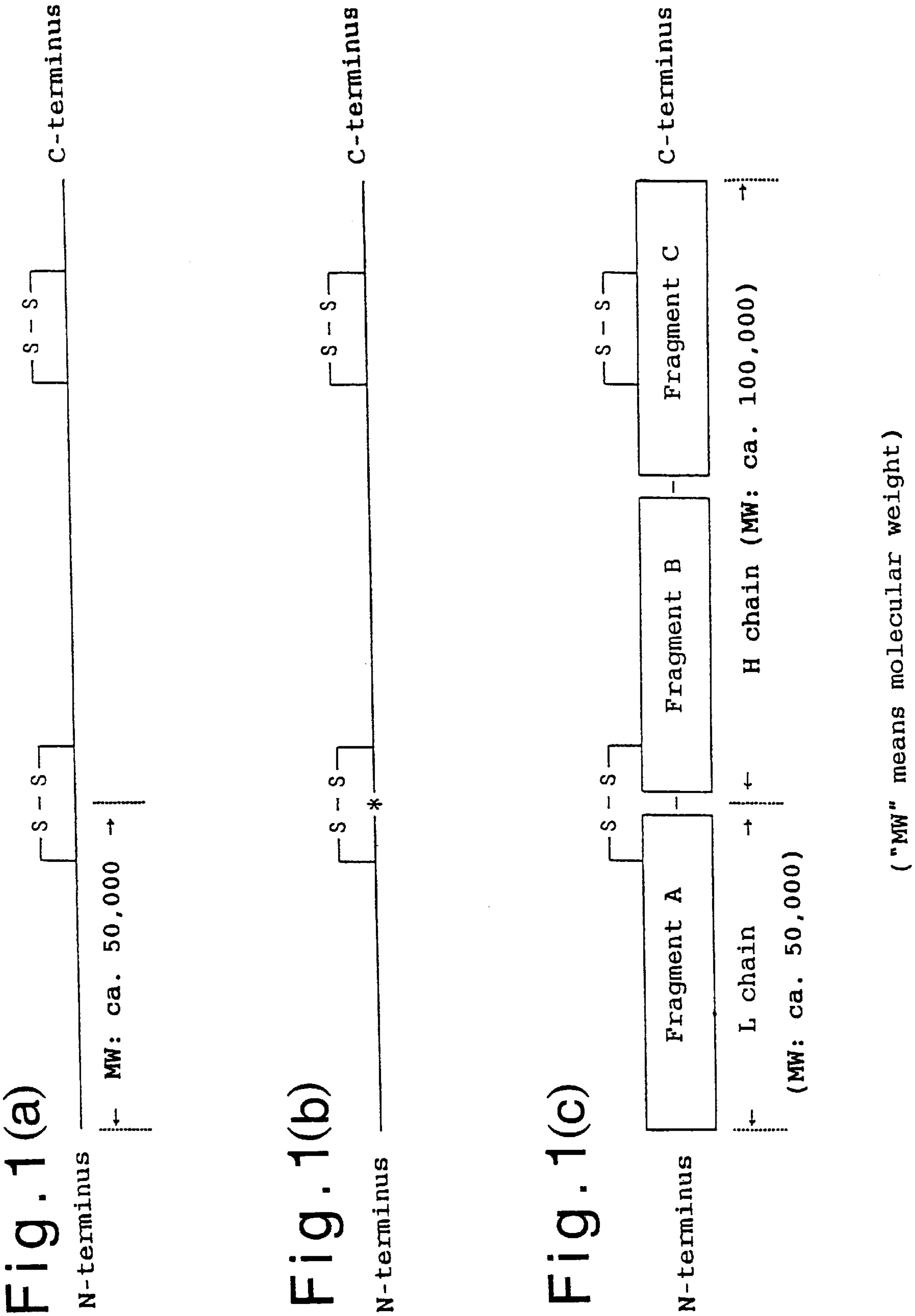
FIG. 1(*a*) is a diagrammatic view of the structure of the whole tetanus toxin molecule used in the present invention.

Further, after the preparation of the whole tetanus toxin molecule and the above-mentioned fragments A, B, C, A-B and B-C, i.e., all the three subunits of tetanus toxin and the complexes of the adjacent subunits, the present inventor examined the differences in functions of these fragments, and the relationship between the subunit structure of tetanus toxin and the mechanism of the toxic action of tetanus toxin, and proposed a "tripartite [A-B·C] molecular model" [see FIG. 1(*c*); Biken Journal, 26, 133–143, 1983; and "Botulinum Neurotoxin and Tetanus toxin", edited by L.

L. Simpson, pp. 69–92 (Chapter 4), Academic Press, 1989].

This tripartite molecular model was accepted as the most appropriate molecular model of tetanus toxin at the 8th International Conference on Tetanus (1988). According to the tripartite [A-B·C] model, fragment C has the role of carrying the tetanus toxin molecule to the central nervous system (letter "C" means "Carrier"), fragment B has the role of binding the tetanus toxin molecule to the presynaptic membrane of the nerve cell and the role of transporting the tetanus toxin molecule into the cytoplasm (letter "B" means "Binding"), and fragment A has the role of exhibiting the toxic activity based on the enzyme activity (letter "A" means "Active") (see "8th International Conference on Tetanus", edited by G. Nistco et al. pp. 170–171, Phythagora Press, Rome-Milan, 1989; Infection and Immunity, 57, 3588–3593, 1989; Toxicon, 27, 385–392, 1989; ibid. 28, 737–741, 1990).

Variety of the Fragments of Tetanus Toxin:

Until 1989, there was no consensus on any of the length, molecular weight and nomenclature of each of the fragments of tetanus toxin among researchers in the world, and this situation gave difficulties in exchange of information and discussions on the structures function relationship of subunits of tetanus toxin among researchers. Therefore, it was desired to establish a common basis for the studies on tetanus toxin by using unitary definitions of fragment models.

In such a situation, the present inventor proposed the above-mentioned tripartite molecular model for the first time. That is, the present inventor pointed out the disadvantages of the absence of a consensus on the lengths, molecular weights and nomenclatures of the tetanus toxin fragments, and the present inventor emphasized the necessity of unitary definitions of fragments and proposed the above models [see the above-mentioned "Botulinum Neurotoxin and Tetanus toxin", edited by L. L. Simpson, pp. 69–92 (Chapter 4)].

It is believed that the reason why a variety of fragments are obtained from the whole tetanus toxin molecule resides not only in the genetic differences of seed strains of *C. tetani* used by different researchers, but also in that there are delicate differences in various operation conditions employed by researchers for obtaining tetanus toxin and fragments thereof, such as the culturing conditions for the seed strain, the autolysis conditions for the cultured cells to obtain the extracellular toxin which has already been converted into a nicked form, and the treating conditions for an extracted intracellular toxin, that is, the conditions for digesting the extracted intracellular toxin by a protease into a nicked form, and the conditions for treating the extracted intracellular toxin with a reducing agent, a denaturing agent, a solubilizing agent or the like, wherein examples of conditions for treating the extracted intracellular toxin include the types of the enzyme and reagents, the treatment temperature, the treatment time, the concentration of the enzyme or reagent, the pH of the treating solution, and the physical conditions for the treatment of the extracted intracellular toxin, i.e., stirring or shaking, or keeping it in a stationary state.

Definition of "FFA" of the Present Invention:

The functional fragment antigen (FFA) of the present invention is a tetanus toxin functional fragment antigen, comprising at least one fragment which is substantially the same as that obtained by a process comprising the steps of splitting at least one peptide bond selected from peptide bonds individually connecting mutually adjacent amino acid residues in a partial amino acid sequence between two cysteine residues participating in forming a disulfide bridge present in the N-terminal of the entire amino acid sequence of a whole tetanus toxin molecule, splitting the disulfide bridge, and splitting non-covalent bonds [as indicated in FIG. 2(*b*)] between groups on the tetanus toxin molecule;

the tetanus toxin functional fragment antigen having:

(a) a molecular weight of from 90,000 to 110,000 as measured by an SDS-polyacrylamide gel electrophoresis method; and (b) an isoelectric point of 7.25±0.5 as measured by an isoelectric focusing method.

As a result of the research by the present inventor, it has been found that various types of N-terminal amino acid sequences of FFA can be obtained [see FIG. 2(*a*)]. In the present invention, it is preferred that the tetanus toxin functional fragment antigen has an N-terminal amino acid sequence selected from the group consisting of the eight amino acid sequences shown in FIG. 2(*a*). Further, the tetanus toxin functional fragment antigen (FFA) of the present invention has an immunopotency which is substantially the same as that of the whole tetanus toxin toxoid. In addition, the tetanus toxin functional fragment antigen (FFA) of the present invention is extremely excellent with respect to the diminution of adverse side effects, as compared to conventional whole tetanus toxin toxoids. The term "immunopotency" means the ability to prevent the occurrence of the symptoms of tetanus. In the present invention, the term "having an immunopotency which is substantially the same as that of the toxoid of the whole tetanus toxin molecule" means that the FFA exhibits a relative potency (ratio of the potency of FFA, relative to the potency of the whole tetanus toxin toxoid) of 1±0.2, as measured by a method in which a vaccine containing FFA and a vaccine containing the whole tetanus toxin toxoid prepared by the method described in Reference Example 14 are subjected to measurement of immunopotency by the parallel line assay using the whole toxin toxoid of a known international unit of potency as a reference and using a challenge toxin of a known $LD_{50}$ (Median Lethol Dose) described in Example 1(5). The results are analyzed by the score method described in Reference Example 15.

Thus, the present invention also provides a single-antigen tetanus vaccine comprising FFA as an active component, such as a plain preparation, an adsorbed preparation or a lyophilized preparation, and a combined vaccine comprising FFA as one of a plurality of active components, such as a DPT combined vaccine, a DT combined vaccine, or a combined vaccine comprising FFA and at least one vaccine antigen selected from the group consisting of vaccine antigens other than FFA, such as Haemophilus influenzae b vaccine antigen, inactivated poliomyelitis vaccine antigen, inactivated hepatitis B vaccine antigen, inactivated Japanese encephalitis vaccine antigen and the like, and a method for producing the above-mentioned vaccines in large quantities.

(1) Seed Microorganisms:

With respect to a microorganism used as a seed culture for obtaining the functional fragment antigen (FFA) of the present invention, there is no particular limitation as long as the microorganism has high toxin-producing ability. Examples of such microorganisms include the substrain of *Clostridium tetani* Harvard strain, and other *C. tetani* strains having substantially the same or higher producing ability for tetanus toxin, as or than that of the Harvard strain. Specifically, for example, it is preferred to use the Biken substrain having high toxin-producing ability (Reference Example 1), obtained by single colony isolation from the Harvard H47 strain, which is a known *C. tetani* strain derived from the Harvard strain [deposited with ATCC (American Type Culture Collection) under the accession No. 10779].

Further, as a seed microorganism, there can also be used a transformant microorganism obtained by a method in which a microorganism, such as yeast, *Escherichia coli, Bacillus subtilis* or the like, is transformed with a gene coding for FFA, using genetic engineering techniques. Specifically, for example, as a seed microorganism there can be used *Escherichia coli* transformed with a large-quantity expression vector having a DNA encoding FFA operably ligated thereto, which transformed *E. coli* is obtained in accordance with the method described in Reference Example 2 mentioned below.

(2) Medium:

Conventional media can be used for culturing the seed microorganism for obtaining FFA. For example, a conventional liquid medium for culturing an anaerobic microorganism can be used for culturing the above-mentioned seed microorganisms. Examples of such liquid media include cooked meat medium, PYG (Peptone, Yeast extract, Glucose) medium, GAM (Gifu Anaerobic Medium) broth, Veal infusion medium, thioglycolate medium, liver-liver broth, RCM (Reinforced Clostridial Medium) broth and DRCM (Differential Reinforced Clostridial Medium) broth. If desired, in order to improve the growth characteristics of the microorganisms and/or the maintenance of the low oxidation-reduction potential, a medium can be modified by replacement, addition or removal of components thereof, or by changing the amount of components thereof. Among these media, liver-liver broth is preferred for use in preparing a seed culture, and a modified Latham medium designed by the present inventor (Reference Example 3) is preferred for use in producing tetanus toxin from the seed culture.

(3) Culture Conditions:

There is no particular limitation with respect to the conditions for culturing the seed microorganism for obtaining FFA. For example, a strain of *C. tetani* having high toxin-producing ability is cultured under culture conditions, in which the incubation temperature is from about 30 to about 37° C., preferably from about 34 to about 36° C., and the incubation time is from about 1 to about 8 days, particularly from about 1 to about 2 days for extracting the intracellular toxin, and particularly from about 4 to about 7 days for harvesting the extracellular toxin.

(4) Starting Materials for the Preparation of FFA:

In the present invention, FFA is prepared using the whole tetanus toxin molecules obtained from the cells cultured as described above. Examples of starting materials for the preparation of FFA include a cell extract (containing an intracellular tetanus toxin) of the microorganisms cultured as described above and a culture supernatant or a culture filtrate (each containing an extracellular tetanus toxin in a nicked form) obtained by a method in which the cultured cells are allowed to undergo autolysis, and the unlysed cells and cell debris contained in the resultant autolysis product are removed by centrifugation or filtration. When it is desired to prepare FFA from intracellular tetanus toxin, it is necessary to split the intracellular tetanus toxin with a protease, such as trypsin or chymotrypsin, thus converting the intracellular tetanus toxin into a nicked form. Therefore, for saving labor in the preparation process and achieving high yield, it is preferred to use, as a starting material, a culture supernatant or a culture filtrate each containing an extracellular tetanus toxin in a nicked form.

(5) Premiminary Purification of Tetanus Yoxin:

The whole tetanus toxin molecule in the starting material can be roughly purified by conventional methods. Examples of such conventional methods include salting out by using ammonium sulfate, alcohol precipitation, adsorption onto and desorption from a gel, and ultrafiltration by using commercially available membranes. In the present invention, the whole tetanus toxin molecule obtained by these preliminary purification methods is referred to as "partially purified whole tetanus toxin".

(6) High Purification of Tetanus Toxin:

The partially purified whole tetanus toxin, obtained by the method described in item (5) above, can be highly purified by, for example, a method using both density-gradient ultracentrifugation and equilibrium density-gradient ultracentrifugation (see Unexamined Japanese Patent Application Laid-Open Specification No. 07-89951), or a method using an appropriate combination of conventional methods, such as ultracentrifugation, gel filtration, ion-exchange chromatography and high performance liquid chromatography. In the present invention, a highly purified whole tetanus toxin molecule obtained by these purification methods (hereinafter, frequently referred to simply as "highly purified tetanus toxin") can be used as a material for preparation of FFA of the present invention. The highly purified tetanus toxin needs to be confirmed with respect to its eligibility for use as whole tetanus toxin molecules. The confirmation of the eligibility can be performed by determining, for example, MLD (Minimum Lethal Dose; Reference Example 4), Lf unit (Unit of flocculation; Reference Example 5), protein content (Reference Example 6), or the like.

(7) Preparation of FFA:

In the present invention, FFA is prepared from the above-mentioned highly purified tetanus toxin. When the highly purified tetanus toxin used for preparation of FFA is prepared from intracellular tetanus toxin, it is first necessary to digest mildly or split the intracellular tetanus toxin with a protease, such as trypsin or chymotrypsin, so as to convert the toxin into a nicked form. Two functionally complementary fragments of tetanus toxin can be prepared by a method comprising the steps of splitting a disulfide bridge present in the N-terminal of the purified tetanus toxin in the nicked form by a reducing agent, and splitting non-covalent bonds between groups on the tetanus toxin molecule by a denaturing agent. Examples of reducing agents include conventional reducing agents, such as sodium thioglycolate, dithiothreitol (hereinafter referred to simply as "DTT"), glutathione, mercaptoethanol, hydrogen sulfide, sodium borohydride, sodium sulfide, ammonium sulfide and the like. As denaturing agents, conventional denaturing agents can be used. Examples of these agents include guanidine thiocyanate, guanidine hydrochloride, urea, sodium dodecyl sulfate and the like. In the present invention, DTT and urea are preferred. With respect to a preferred manner of the use of DTT, for example, the final concentration of DTT in a solution containing the toxin protein in an amount of from about 1 to about 10 mg/ml is generally in the range of from 10 to 200 mM, preferably from 50 to 150 mM, and the reaction is conducted at 15 to 35° C. for 20 to 180 minutes. With respect to a preferred manner of the use of urea, for example, the final concentration of urea in a solution containing the toxin protein in an amount of from about 1 to about 10 mg/ml is generally in the range of from 0.5 to 10 M, preferably from 1 to 5 M, and the reaction is conducted at 5 to 35° C. for 10 seconds to 15 minutes. Each of these reagents is added to the starting material so that the concentration of the reagent falls within the above-mentioned respective concentration range. In the present invention, DTT is used in the form of a solution (see Reference Example 8; hereinafter, this solution is referred to as "DTT Tris buffer"), and the solution is added to the starting material in an amount about 5 to about 50 times by volume the amount of the starting material, to react DTT with tetanus toxin. Urea is used in the form of a saturated solution or directly in the form of crystals.

As a result of the above-mentioned treatments with DTT and urea, the whole tetanus toxin molecule in the nicked form is split to obtain a solution containing FFA. By diluting the solution containing FFA to thereby lower the concentration of urea, FFA can be obtained as a highly purified tetanus toxin fragment by fractionation or separation using an absorbance at 280 nm as an index (see Reference Example 7). The purification can be performed by, for example, a combined method using both density-gradient ultracentrifugation and equilibrium density-gradient ultracentrifugation (see Unexamined Japanese Patent Application No. 07-89951), SDS-PAGE (Sodium Dodecyl Sulfate-Polyacrylamide Gel Electrophoresis), gel filtration, membrane filtration, ion-exchange chromatography, high performance liquid chromatography and the like. By these purification methods, two fractions of different molecular weights, corresponding to two peaks appearing at 280 nm, are obtained, and FFA is found in the fraction of the larger molecular weight. This fraction containing FFA is used as an active component for an FFA tetanus vaccine. The whole tetanus toxin molecule can be prepared according to the method described below (Reference Example 13). The molecular weight, antigenic specificity, amino acid sequence and the like of each of the whole tetanus toxin molecule and FFA can be determined by, for example, SDS-PAGE (Reference Example 10), a precipitation reaction in gel (Reference Example 11) and a method using a peptide sequencer (Reference Example 12).

(8) Stabilization of FFA:

In the FFA of the present invention, a whole or most of the fragment A region, which is the active site exhibiting the toxicity, is absent, so that the FFA of the present invention has no toxicity. Therefore, the FFA as such can be used as a toxoid without detoxification. However, for stabilizing the stereochemical structure of FFA as an antigen, it is preferred to perform a stabilization (fixation) of the tetanus toxin FFA. Examples of fixatives (fixing or stabilizing reagent) include conventional detoxifying agents, such as formalin, glutaraldehyde, β-propiolactone and the like. For example, when formalin is used as a fixative, it is preferred that the volume ratio of formalin to the FFA solution is approximately within the range of from 0.0004 to 0.7% (v/v). The fixation temperature is approximately within the range of from 3 to 37° C. and the fixation time is approximately within the range of from 5 to 180 days. When there is a danger that the antigenecity of FFA is deteriorated by the fixation, the fixation conditions are rendered moderate by lowering the concentration of the fixative, lowering the fixation temperature or adding neutral amino acids, such as glycine and serine, or basic amino acids, such as lysine and arginine. When free formaldehyde remains in the solution after the fixation, if desired, it can be neutralized by addition of sodium hydrogensulfite in an equivalent amount to the amount of the formaldehyde, or can be removed by filtration using a membrane or by dialysis. After the fixation treatment, the FFA solution is stored at 4° C. for subsequent use as a bulk solution of tetanus toxin vaccine for preparing a tetanus vaccine. After the fixation treatment, the treated whole tetanus toxin molecule and treated FFA are referred to as a "whole tetanus toxin toxoid" and an "FFA toxoid", respectively.

(9) Preparation of FFA Tetanus Vaccine:

The FFA toxoid bulk solution obtained in item (8) above can be diluted so as to obtain a vaccine comprising the FFA toxoid in an effective immunogenic amount. For example, the bulk solution can be diluted with an isotonic solution of salts, or with buffer or a medium for tissue culture so that the protein content of the vaccine becomes from 20 to 200 μg for a single-antigen toxoid, or 8 to 80 μg for an adsorbed toxoid.

When the bulk solution is diluted as mentioned above, a stabilizer for increasing the heat resistance of the vaccine or an adjuvant as a supplementary agent for increasing the immunopotency can be added to the vaccine solution. It is preferred that the stabilizer is added to the vaccine in an amount of from 0.01 to 10 % (w/v), and the adjuvant is added in an amount of from 0.1 to 50 mg per ml of the vaccine. Examples of stabilizers include saccharides, amino acids, gelatin hydrolyzate, human albumin and the like. Examples of adjuvants include gels capable of effecting sustained release of antigens, such as calcium phosphate, aluminum phosphate, aluminum sulfate, alumina, bentonite and the like; and antibody production inducing agents, such as muramyldipeptide derivatives, oils and the like.

Subsequently, the single-antigen vaccine or adsorbed vaccine is dispensed into small containers, such as ampuls or vials. Then, the containers are sealed hermetically, for example, by fusion sealing, and the sealed vaccine is provided as a plain or adsorbed preparation. When the vaccine is lyophilized after dispensation, the vaccine can be provided as a lyophilized preparation. Further, the vaccine can be provided in the form of a combined vaccine preparation, such as a DT binary vaccine, a DPT ternary vaccine, a quaternary vaccine or the like.

Each of these preparations is subjected to various tests to verify the eligibility for use as a toxoid or a vaccine. That is, each of these preparations is subjected to various tests on effectiveness, safety and homogeneity in accordance with a relevant provision (such as a provision entitled "tetanus toxoid", a provision entitled "adsorbed tetanus toxoid", a provision entitled "diphtheria-tetanus combined toxoid", or a provision entitled "diphtheria-pertussis-tetanus combined vaccine") in the Notification No. 217 of the Japanese Ministry of Health and Welfare: "Seibutsugakuteki Seizai Kijun (Minimum Requirements for Biological Products), to thereby verify its eligibility for use as a vaccine. Only the verified preparations are put to practical use. With respect to the manner of administration, for example, a preparation is usually administrated by subcutaneous or intramuscular injection in an amount of 0.5 ml per person. In the case of a lyophilized preparation, before use, it is dissolved in sterile distilled water so as to obtain a solution having the original volume before lyophilization.

(10) Measurement of Immunopotency of FFA Tetanus Vaccine:

The immunopotency of FFA tetanus vaccine of the present invention is measured using immunized animals (guinea pigs or mice) by a potency assay using a challenge toxin of a known $LD_{50}$ (Median Lethal dose), or an assay of toxin-neutralizing activity of antisera, in accordance with the provision entitled "tetanus toxoid" or the provision entitled "adsorbed tetanus toxoid" in the Notification No. 217 of the Japanese Ministry of Health and Welfare: "Seibutsugakuteki Seizai Kijun (Minimum Requirements for Biological Products)". In addition to the above-mentioned tests, in the present invention, the relative immunopotency of FFA to that of the whole tetanus toxoid is measured by performing a further potency assay using a challenge toxin, wherein the score method (Reference Example 15) is employed.

(11) Animal Tests on the Adverse Side Effects of FFA Tetanus Toxoid:

Animal tests on the side effects of the FFA tetanus vaccine of the present invention can be conducted in accordance with conventional methods. Examples of animal tests which can be employed for evaluating the adverse side effects of tetanus toxoid include the passive cutaneous anaphylaxis (PCA) test using rats which is based on an immediate type allergic reaction, the footpad reaction test using mice which is based on a delayed type allergic reaction, and the intradermal reaction test using guinea pigs (Reference Example 16) which test is based on a delayed type allergic reaction.

BEST MODE FOR CARRYING OUT THE INVENTION

Hereinbelow, the present invention will be described in more detail with reference to the following Examples and Reference Examples, but they should not be construed as limiting the scope of the present invention.

In the following Reference Examples, the guidelines for carrying out the present invention are specifically shown.

REFERENCE EXAMPLE 1

Isolation of a Single Colony of a *C. tetani* Strain having High Toxin-producing Ability:

Colonies of *C. tetani* Harvard A47 strain are formed on a plate of Zeissler's blood agar [prepared by adding glucose and defibrinated bovine blood to a commercially available non-modified agar medium in such amounts as would give a final glucose concentration of 2% (w/v) and a final defibrinated bovine blood concentration of 20% (v/v), followed by mixing], and the formed colonies are individually inoculated into a modified Latham medium (see Reference Example 3 below) and incubated to obtain cultures. With respect to each of the obtained cultures, the Lf value is measured in accordance with the method as described in Reference Example 5 below. From the above-mentioned colonies, the colony used for the culture having the highest Lf value is used as a Biken substrain of the *C. tetani* Harvard A47 strain, which has high toxin-producing ability.

REFERENCE EXAMPLE 2

Preparation of Transformants having High Toxin-producing Ability for FFA:

A DNA of tetanus toxin gene [see EMBO JOURNAL, 5(10), 2495–2502, 1986 and Nucleic Acid Research 14(19), 7809–7812, 1986] is digested with the restriction enzymes, thereby obtaining a 2.7 kb DNA fragment (Stu I-Bsp HI) coding for FFA. The obtained DNA fragment is inserted into and ligated to pSN508 [which is a vector capable of a large-quantity expression in *E. coli* (see U.S. Pat. No. 4,703,005)] to obtain a recombinant expression vector. Then, the obtained recombinant expression vector is introduced into *E. coli*strain CSH26 to form transformants having high toxin-producing ability for FFA. When the production of the FFA is conducted by culturing the above-mentioned transformants, it is not necessary to perform the treatments described below, such as a protease digestion of the whole tetanus toxin molecule, and a treatment using dithiothreitol or urea, but purification is necessary.

REFERENCE EXAMPLE 3

Composition of the Modified Latham Medium (per 1 liter of the medium):

| | |
|---|---|
| Polypeptone | 20 g |
| Bovine heart extract | 10 g |
| Glucose | 8.0 g |
| Sodium chloride | 2.5 g |
| Magnesium sulfate (heptahydrate) | 0.1 g |
| Cystine | 0.125 μg |
| Calcium pantothenate | 1.0 mg |
| Uracil | 1.25 mg |
| Nicotinic acid | 0.25 mg |
| Thiamine | 0.25 mg |
| Riboflavin | 0.25 mg |
| Pyridoxine | 0.25 mg |
| Biotin | 2.5 μg |
| Vitamin $B_{12}$ | 0.05 μg |
| Folic acid | 100 μg |
| Iron(III) chloride (hexahydrate) | 32 mg |
| Iron sulfate (heptahydrate) | 0.2 g |
| (The pH was adjusted to 7.0 using 7N NaOH) | |

REFERENCE EXAMPLE 4

MLD (Minimum Lethal Dose):

0.1 to 0.5 ml of each of dilutions of the tetanus toxin-containing solution which have been prepared by successively diluting tetanus toxin at logarithmic intervals of $10^{0.5}$ is individually injected subcutaneously or intramuscularly to OF1 mice (weighing 20 to 25 g) at the of the thigh of the left hind leg. MLD is determined, based on the dose (log. of dose)-response (time to death) curve [see "Proceedings of the 6th International Conference on Tetanus (Lyon, 1981)" pp. 21–32].

REFERENCE EXAMPLE 5

Lf unit (Unit of Flocculation):

The Lf value of a toxin solution can be measured by the Ramon's method. (Biken Journal, 7, 137–152, 1964). 1 Lf of the toxin, which is the amount of the toxin which reacts with 1 unit of the antitoxin, is measured. Also, the measurement of the above-mentioned Lf value can be conducted using SRID (Single Radial Immunodiffusion) (see Immunochemistry, 2, 235–254, 1965).

REFERENCE EXAMPLE 6

Measurement of Protein Content:

The protein content is measured in accordance with the "modified method of Lowry et al." in which the color reaction of a protein and a phenol reagent is evaluated by colorimetry. Hereinafter, this method is simply referred to as a "phenol reagent method".

REFERENCE EXAMPLE 7

Identification of Protein Fractions and Comparison on Protein Concentrations Between the Protein Fractions:

The identification of protein fractions and the comparison on protein concentrations between the protein fractions are conducted by measuring the absorbance of ultraviolet rays having a wave length of 280 nm (hereinafter, referred to as an "absorbance at 280 nm") of a sample.

REFERENCE EXAMPLE 8

Preparation of a DTT-Tris Buffer (100 mM):

A DTT-Tris buffer is prepared by mixing 50 mM tris (hydroxymethyl)aminomethane-HCl (hereinafter, simply referred to as "Tris"), 1 mM ethylenediamine-tetraacetate-4 Na (hereinafter, simply referred to as "EDTA") and 100 mM DTT. The pH of the DTT-Tris buffer is adjusted to 8.2 using 1/10 M HCl.

REFERENCE EXAMPLE 9

Preparation of a Phosphate Buffer:

A phosphate buffer is prepared by mixing equal molar amounts of disodium monohydrogenphosphate and potassium dihydrogenphosphate solutions. The amounts of the solutions to be mixed are appropriately chosen so that the resultant phosphate buffer has a desired pH value.

REFERENCE EXAMPLE 10

Measurement of the Molecular Weights of Proteins by Using SDS-PAGE:

In the SDS-PAGE, an SDS-PAGE gel having a gel content of 7.5% (w/v), 7.0% (w/v) (containing 2M urea), 5.0% (w/v) or the like can be used. As a buffer solution, for example, 10 mM Tris-77 mM glycine buffer (pH 8.6) can be used. After the electrophoresis, the gel is stained using Coomassie brilliant blue. The molecular weight of each of the proteins is individually determined from the ratio of the migration distance of the sample protein to the migration distance of the marker dye or the protein having known molecular weight. As a result of the measurements conducted in accordance with the above method, it is found that the molecular weights ($\times 10^4$) of the FFA and the whole tetanus toxin molecule are 100,000 and 150,000, respectively.

REFERENCE EXAMPLE 11

Determination of the Antigenic Specificity by Using Double Immunodifusion:

The antigenic specificity is determined by the method of Ouchterlony using 1% (w/v) agarose in 50 mM Tris-0.6 M Glycine buffer (containing 1 mM EDTA; pH 8.5) and horse anti-tetanus toxin serum from which nonspecific antibodies are removed. A cross-reaction of antigenicity is observed between the FFA and the whole tetanus toxin molecule.

REFERENCE EXAMPLE 12

Determination of the Amino Acid Sequence of the FFA:

The determination of the amino acid sequence of the FFA is conducted using an automatic amino acid sequencer, such as Applied Biosystem Procise Type 492 manufactured and sold by Perkin Elmer, U.S.A. The FFA obtained in Example 1 below has N-terminal amino acid sequence (7) of FIG. 2(*a*), and the FFA obtained in Example 7 below has N-terminal amino acid sequence (4) of FIG. 2(*a*). Further, by appropriately choosing the conditions for cultivation of *C. tetani*, an FFA having N-terminal amino acid sequence (8) of FIG. 2(*a*) can be obtained. FFA's respectively having N-terminal amino acid sequences (1) to (3) and (6) of FIG. 2(*a*) can be prepared from the intracellular tetanus toxin by appropriately choosing the conditions for digesting the intracellular tetanus toxin molecule with trypsin to convert the toxin molecule to a nicked form thereof, such as an enzyme concentration, a reaction time and a reaction temperature. An FFA preparation having N-terminal amino acid sequence (5) of FIG. 2(*a*) can be prepared by digesting the intracellular tetanus toxin molecule with chymotrypsin to convert the toxin molecule to a nicked form thereof. Thus, in the present invention, 8 different types of FFA's respectively having N-terminal amino acid sequences (1) to (8) of FIG. 2(*a*) can be obtained. These 8 types of FFA's may be used as an active component of a tetanus vaccine individually or in combination.

REFERENCE EXAMPLE 13

Determination of the Isoelectric Point of FFA:

The isoelectric point of FFA is determined by an isoelectric focusing method using a commercially available gel, for example, a gel manufactured and sold under the tradename "Phast Gel IEP 3-9" by Pharmacia Biotech, Sweden. As a result of the measurements conducted in the Examples in accordance with the above method, it was found that the FFA of the present invention has an isoelectric point within the range of 7.25±0.5.

REFERENCE EXAMPLE 14

Preparation of the Whole Tetanus Toxin Molecule:

The seed culture of the *C. tetani* strain obtained in Reference Example 1 is inoculated into a culture medium described in Reference Example 3 for 44 hours and the bacterial cells are harvested by centrifugation at 10,000×g at 4° C. for 25 minutes. 1 M NaCl solution containing 0.1 M sodium citrate is added in an amount of 1/30 volume of the cell culture to extract the intracellular toxin by gentle agitation. The resultant mixture is stirred at 4° C. overnight to extract tetanus toxin, and then is centrifuged at 10,000×g at 4° C. for 30 minutes to remove cells and cell debris. Using the resultant supernatant as a starting material, the toxin is purified in substantially the same manner as in Example 1 below to obtain a purified whole tetanus toxin preparation.

REFERENCE EXAMPLE 15

Score Method for Evaluating Immunopotency:

Relative potency of tetanus toxoid is evaluated using a score method. Illustratively stated, animals for immunological experiment, which have been injected with tetanus vaccine, are challenged with toxin, and observed over a week for the symptoms of tetanus. The severity of the symptoms was evaluated in accordance with the following criteria by the score method:

| Results | Score |
| --- | --- |
| The animal dies on the 1st day: | 0 |
| The animal dies on the 2nd day: | 1 |
| The animal dies on the 3rd day: | 2 |
| The animal dies or exhibits serious symptoms (such as a tonic convulsion, a difficulty in walking and a respiratory distress) between the 4th and 7th day: | 3 |
| The animal survives through one week with slight symptoms [such as a local paralysis of the abdominal muscle on a side opposite to the side on which the injection had been made (this symptom is checked by observing the animal hung by its tail)]: | 4 |
| The animal survives through one week without any symptom: | 8 |

The obtained scores are analyzed by a computer using a software designed for statistical analysis for the parallel-line assay, in which the correlation analysis of the scores is conducted in terms of uniformity, linearity and parallelity to evaluate the relative immunopotency of the tetanus toxoid to that of the standard tetanus whole toxin toxoid of a known international units.

REFERENCE EXAMPLE 16

Intradermal Reaction Using Guinea Pigs:

Three groups of guinea pigs are sensitized by intramuscular injection with 1 ml of tetanus vaccine (10 μg protein/ml) per 1 guinea pig, wherein the above-mentioned three groups of guinea pigs are sensitized with (1) commercially available partially purified whole toxin toxoid, (2) purified whole toxin toxoid and (3) FFA vaccine, respectively. After 4 weeks from the sensitization, the back of each of the guinea pigs is shaved and then, the guinea pigs are individually injected intradermally with 0.1 ml of the above-mentioned tetanus toxoid onto the back thereof. The protein concentration of the tetanus toxin solution is varied (32.0, 10.0 and 3.2 μg) depending on the group to which a guinea pig belongs. 24 hours after the injection, with respect to each of the guinea pigs, the portion which has been injected is examined to see whether or not a skin reaction, an erythema, an induration and/or a necrosis occurs. When the occurrence of an erythema is observed, the diameter of the erythema is measured.

EXAMPLE 1

(1) Production and Purification of the Whole Tetanus Toxin Molecule (nicked form)

Into each of 20 tubes (diameter: 6 cm; height: 38 cm) containing 450 ml of a modified Latham medium (see Reference Example 3), 5 ml of the seed culture of a Biken substrain of the *C. tetani* Harvard A47 strain (see Reference Example 1) was inoculated. The tubes with loose cotton plugs were incubated at 35° C. for 5 days until the cultures became clear. These cultures were centrifuged at 10,000×g at 4° C. for 30 minutes to obtain clean culture supernatants.

8.5 liters of the culture supernatants thus obtained as starting materials were filtered and used for purification of whole tetanus toxin molecules (nicked form).

A saturated solution (at 25° C.) of ammonium sulfate (pH 7.0) was added to and mixed with the starting material in an ice-water bath to salt out a fraction having an ammonium sulfate saturation of 20% to 40%. The obtained fraction was suspended in 65 ml of 0.06 M phosphate buffer (pH 7.5, 4° C.) (see Reference Example 9) to obtain a suspension having an ammonium sulfate saturation of 40%. The obtained suspension was subjected to centrifugation at 15,000×g at 4° C. for 30 minutes to obtain a precipitate. The obtained precipitate was washed by resuspending the precipitate in 22 ml of the above-mentioned phosphate buffer, and the resultant was subjected to centrifugation under the same centrifugation conditions as mentioned above. The washed precipitate was dissolved in 22 ml of 0.1 M phosphate buffer (pH 7.5, 4° C.) and subjected to ultracentrifugation at 100,000×g at 4° C. for 2 hours to remove the precipitated residue, thereby obtaining 20 ml of a supernatant. The obtained supernatant was filtered through Acrodisc membrane (pore diameter: 0.2 μm) (manufactured and sold by Gelman Co. Ltd., Germany), and the resultant filtrate of partially purified toxin was subjected to gel filtration by using Ultrogel AcA 34 column (inner diameter: 2.5 cm, length: 100 cm) (manufactured and sold by LKB-Pharmacia, Sweden) equilibrated with 0.1 M phosphate buffer (pH 7.5). In the gel filtration, elution was carried out at 4° C. using the above-mentioned phosphate buffer (flow rate: 9 ml/hr), and the resultant eluate was fractioned into 1 ml fractions. With respect to each of the fractions, an absorbance at 280 nm (see Reference Example 7) was measured. The fractions having a high absorbance were pooled, thereby obtaining a gel filtration eluate in a total volume of 5 ml.

With respect to the obtained eluate, the measurement of the protein content in accordance with the phenol reagent method (see Reference Example 6), the measurement of MLD per 1 mg of protein (see Reference Example 4) and the measurement of Lf per 1 mg of protein (see Reference Example 5) were conducted. As a result, the protein content of the eluate was 60 mg/ml, Lf was 400 and MLD was $3.5\times10^7$.

Further, 0.2 ml of the eluate was subjected to high performance liquid chromatography (HPLC) using TSK G3000 SW column (inner diameter: 0.75 cm, length: 60 cm) (manufactured and sold by Tosoh Corp., Japan) equilibrated with 0.1 M phosphate buffer (pH 6.8), in which elution was carried out using the above-mentioned phosphate buffer (flow rate: 0.6 ml/minute) to thereby obtain fractions. The absorbance at 280 nm of each of the fractions was measured. As a result, a single sharp peak was observed, which indicates that the whole tetanus toxin molecule was highly purified. In the preparation of FFA described below, the eluate obtained above was used as a solution of a highly purified entire length tetanus toxin molecule (nicked form) (i.e., a highly purified tetanus toxin solution).

(2) Preparation of FFA 18 ml of a DTT-Tris buffer (see Reference Example 8) was added to 2 ml of the highly purified tetanus toxin solution, followed by mixing. The resultant mixture was reacted at 25° C. for 60 minutes to reduce the disulfide bridge present in the whole tetanus toxin molecule. The resultant mixture was treated with urea by adding 4.8 g of a solid urea to the mixture, followed by mixing to dissolve the solid urea in the mixture (final urea concentration: 4 M). To the resultant was added 20 ml of 50 mM Tris buffer (containing 0.6 M glycine, 1 mM EDTA and 1 mM DTT; pH 8.5) and the resultant mixture was condensed using Amicon Ultrafiltration System (manufactured and sold by Grace Company, U.S.A.)," thereby obtaining 3 ml of a condensate. The obtained condensate was subjected to gel filtration by using Ultrogel AcA 44 column (inner diameter: 1.5 cm, height: 90 cm) equilibrated with 50 mM Tris buffer (containing 0.6 M glycine, 1 mM EDTA and 1 mM DTT and 2 M urea; pH 8.5). In the gel filtration, elution was carried out using the above-mentioned 50 mM Tris buffer (flow rate: 5 ml/hr) and the resultant eluate was fractioned into 1.2 ml fractions. With respect to each of the fractions, the absorbance at 280 nm was measured. As a result, two peaks (peak 1 and peak 2) were observed. From the obtained fractions including two fractions each exhibiting a peak at 280 nm (i.e., a peak 1 fraction and a peak 2 fraction, wherein the peak 1 fraction was obtained earlier than the peak 2 fraction), a set of 5 fractions (total amount: 6 ml) successively obtained starting from the peak 1 fraction and another set of 5 fractions (total amount: 6 ml) successively obtained starting from the peak 2 fraction were collected to obtain a collected fraction 1 and a collected fraction 2, respectively.

Each of the highly purified tetanus toxin solution, the collected fraction 1 and the collected fraction 2 was subjected to SDS-PAGE (see Reference Example 10) for determination of the approximate molecular weight and to gel precipitation reaction (see Reference Example 11) for determination of the antigenicity. As a result, the molecular weights of the purified tetanus toxin, the collected fraction 1 and the collected fraction 2 were approximately 150,000, 100,000 and 50,000, respectively. With respect to the antigenicity, the cross-reaction of the antigenicity was observed between the highly purified tetanus toxin solution and each of the collected fraction 1 and the collected fraction 2, whereas no cross-reaction was observed between the collected fraction 1 fraction and the collected fraction 2, which indicates that these two types of collected fractions had completely different antigenicities. Further, the protein contents of the collected fraction 1 and the collected fraction 2 were determined by the phenol reagent method. The protein contents of the collected fraction 1 and the collected fraction 2 were 15 mg/ml and 8 mg/ml, respectively. From the above results, it was confirmed that the collected fraction 1 contains FFA. In the operations described below, the collected fraction 1 was used as an FFA solution.

(3) Stabilization of the FFA 4 ml of the FFA solution was dialyzed against 1/15 M phosphate buffer (pH 7.8) at 4° C. overnight. After completion of the dialysis, the above-mentioned phosphate buffer was added to and mixed with the dialyzed FFA solution to thereby obtain a solution having a total volume of 380 ml. 20 ml of 500 mM lysine solution was added to the above-mentioned FFA solution so that the protein content of the FFA solution became 600 μg/ml. To the resultant FFA solution was added formalin in an amount such that the final formalin concentration became 0.2% (v/v), and the resultant mixture was subjected to incubation at 37° C. for 14 days to stabilize the FFA. Then, the stabilized FFA was dialyzed against a 0.85% (w/v) NaCl solution at 4° C. overnight to remove formaldehyde and lysine, and the dialyzate was filtered through Acrodisc membrane (pore diameter: 0.22 μm) for sterilization, thereby obtaining 380 ml of a filtrate. The obtained filtrate was stored at 4° C., and was used as a bulk FFA tetanus vaccine solution described below.

(4) Preparation of a Sample FFA Tetanus Vaccine

The bulk FFA tetanus vaccine solution was diluted with a 0.85% (w/v) NaCl solution so as to obtain a diluted solution having a final protein concentration of 50 μg/ml. An equivolume of $Al(OH)_3$ gel suspension [$Al(OH)_3$ content: 2 mg/ml] was added to the obtained diluted solution, followed by mixing. The resultant mixture was allowed to stand at 4° C. overnight so that the FFA was adsorbed on the $Al(OH)_3$ gel, thereby obtaining a sample vaccine. With respect to the obtained sample vaccine, the activities thereof (immunopotency) and the safety thereof (toxicity or adverse side effects) were evaluated as described below.

(5) Evaluation of the Immunopotency of the Sample FFA Tetanus Vaccine

The evaluation of the immunopotency of the sample FFA tetanus vaccine was conducted by experiments using mice. As a control, another vaccine was prepared in substantially the same manner as in the items (3) and (4) above, except that the solution of the whole tetanus toxin molecule prepared in Reference Example 14 was used. With respect to each of the sample vaccine and the control vaccine, serial 2.5-fold dilution with a 0.85% (w/v) NaCl solution was conducted to obtain dilutions having different dilution ratios, which were administered to mice as described below, wherein at least three dilutions had dilution ratios such that the dilutions exhibited dose-response relationships falling within the linear region of the dose-response curve. Using the obtained vaccine dilutions (i.e., sample vaccine dilutions and control vaccine dilutions), the immunization of mice was conducted as follows. The sample vaccine dilutions (each having the amount of 0.5 ml) were, respectively, administered to 10 randomly selected ddy/s female mice (each weighing 22 to 26 g) by subcutaneous injection to the inside of the thigh of the left hind leg. Four weeks after the injection, each of the immunized mice was challenged with 100 $LD_{50}$ standard toxin (Lot TA-4B) (provided by the National Institute of Health of Japan) by subcutaneous injection. The above operations were also conducted using the control vaccine dilutions instead of the sample vaccine dilutions. After the above operations, observations were made over a week as to whether or not the mice were alive, and as to the symptoms of the mice which were alive. Results of the observations were evaluated by the score method (see Reference Example 15). The obtained scores were analyzed with respect to variance and correlation by a computer using a software for the statistical analysis. From the results of the statistical analysis, the relative immunopotency of the sample FFA tetanus vaccine (the ratio of the immunopotency of the sample vaccine relative to the immunopotency of the vaccine comprising the whole tetanus toxin toxoid, wherein the immunopotency of the control vaccine is defined as 1.0) was calculated. The above experiment was repeated four times, and the obtained values of the relative immunopotency were statistically analyzed by a computer. Results are shown in Table 1. The immunopotency of the sample FFA tetanus vaccine was substantially the same as that of the control vaccine comprising the whole tetanus toxin toxoid.

(6) Experiments Using Guinea Pigs to Evaluate the Degree of Adverse Side Reactions Caused by the Intradermal Reaction of the Sample FFA Tetanus Vaccine.

The intradermal reactions were conducted using guinea pigs (std. Hartley, weighing 300 to 350 g, 5 weeks old, female) (obtained from Japan SLC, Inc., Japan) in accordance with the method described in Reference Example 16. The sensitization of the guinea pigs was conducted as follows. As antigens for sensitizing the guinea pigs, use was made of the sample FFA tetanus vaccine (FFA), a commercially available tetanus toxoid presumably containing a whole tetanus toxin toxoid (conventional toxoid) and the vaccine comprising the purified whole tetanus toxin toxoid (whole toxin toxoid). Each of these antigens was diluted using a 0.85% (w/v) NaCl solution so that the final protein concentration and the final $Al(OH)_3$ concentration became 10 μg/ml and 0.2 mg/ml, respectively, to thereby obtain three types of antigen dilutions. The guinea pigs were randomly divided into nine groups each consisting of three guinea pigs, and the above-obtained three types of the antigen dilutions were, respectively, administered to three guinea pigs of each of the nine groups. After completion of the sensitization period (4 weeks), the sensitized guinea pigs were challenged by the above-mentioned antigens by the following method. With respect to each of the above-mentioned antigens, three types of dilutions thereof respectively having final protein concentrations of 3.2, 1.0 and 0.32 μg/ml were prepared using a 0.85% (w/v) NaCl solution. The resultant nine types of dilutions (consisting of three types of dilutions of the FFA, three types of dilutions of the conventional toxoid and three types of dilutions of the whole toxin toxoid) were administered to the guinea pigs so that the guinea pigs belonging to the same group took the administration of the same type of dilution, wherein the dose of each of the dilutions was 0.1 ml. As a control, 0.1 ml of a 0.85% (w/v) NaCl solution was intradermally injected to each of three guinea pigs which had respectively been sensitized with the above-mentioned antigens in substantially the same manner as mentioned above. The results are shown in Table 2. With respect to each of the guinea pigs which had taken the administration of the sample FFA tetanus vaccine, the occurrence of the intradermal reaction was either undetectable or markedly slight as compared to that of the guinea pigs which had taken the administration of the conventional vaccine and the guinea pigs which had taken the administration of the vaccine comprising the whole tetanus toxin toxoid.

EXAMPLE 2

(1) Preparation of the Bulk FFA Tetanus Vaccine Solution 0.5 Liter of a seed culture of a Biken substrain of *C. tetani* Harvard A47 strain was inoculated in 80 liters of the modified Latham medium contained in a stainless steel tank having a volume of 100 liters (diameter: 60 cm, height: 50 cm). The tank was sealed by means of a silicone sheet, and the seed culture was incubated at 35° C. for 6 days to thereby obtain a culture. The obtained culture was filtered through a celite-filter paper for sterilization, thereby obtaining 75 liters of a filtrate. The obtained filtrate was concentrated using the "pericon cassette system" (manufactured and sold by Millipore, U.S.A.), thereby obtaining 7 liters of a condensate. Using the obtained condensate as a starting material, the purification of the whole tetanus toxin molecule, the preparation of the FFA and the stabilization of the FFA were performed in substantially the same manner as in Example 1, thereby obtaining 450 ml of a bulk FFA tetanus vaccine solution having a protein concentration of 600 μg/ ml.

(2) Production of an FFA Tetanus Plain vaccine Preparation

The bulk FFA tetanus vaccine solution obtained above was diluted using 1/75 M phosphate buffer (pH 6.5) so that the final protein concentration of the vaccine preparation would become 60 μg/ml. To the resultant dilution were individually added sucrose, L-arginine and Haemaccel (manufactured and sold by Hoechst Aktiengesellschaft, Germany) in this order in amounts such that the final concentrations of sucrose, L-arginine and Haemaccel became 3% (w/v), 1% (w/v) and 2% (w/v), respectively, followed by mixing to obtain a single-antigen vaccine preparation. The obtained preparation was dispensed in glass vials each having a volume of 1 ml, so that each vial contained 0.6 ml of the preparation, and then, the vials were sealed. The obtained single-antigen vaccine preparation was subjected to various tests in accordance with a provision entitled "tetanus toxoid" in the Notification No. 217 of the Japanese Ministry of Health and Welfare: "Seibutsugakuteki Seizai Kijun (Minimum Requirements for Biological Products)". As a result, the obtained preparation was verified as a qualified vaccine.

EXAMPLE 3

Production of an Adsorbed FFA Tetanus Vaccine Preparation

The bulk FFA tetanus vaccine solution obtained in Example 2 was diluted using 1/40 M phosphate buffer (pH 6.0) so that the final protein concentration of the vaccine preparation became 60 $\mu$g/ml. To the resultant dilution was added an aluminum phosphate gel in an amount such that the final aluminum phosphate gel concentration of the vaccine preparation became 0.2 ml/ml, thereby obtaining a mixture. The obtained mixture was stirred at 4° C. for 5 hours so as to adsorb the FFA on the aluminum phosphate gel. The resultant mixture was subjected to centrifugation at 2000 rpm for 20 minutes at 4° C. to collect the gel. The collected gel was suspended in 1/75 M phosphate buffer (pH 6.5). To the resultant suspension were added sucrose, L-arginine and Haemaccel (manufactured and sold by Hoechst Aktiengesellschaft, Germany) in this order in amounts such that the final concentrations of sucrose, L-arginine and Haemaccel became 3% (w/v), 1% (w/v) and 2% (w/v), respectively, followed by mixing to obtain an adsorbed FFA tetanus vaccine preparation. The obtained preparation was dispensed in glass vials having a volume of 1 ml so that each vial contained 0.6 ml of the preparation, and then, the vials were sealed. The obtained adsorbed FFA tetanus vaccine preparation was subjected to various tests in accordance with a provision entitled "adsorbed tetanus toxoid" in the Notification No. 217 of the Japanese Ministry of Health and Welfare: "Seibutsugakuteki Seizai Kijun (Minimum Requirements for Biological Products)". As a result, the obtained preparation was verified as a qualified vaccine.

EXAMPLE 4

Production of an Adsorbed DPT Combined Vaccine Preparation Using an FFA Tetanus Vaccine An adsorbed FFA vaccine was prepared in substantially the same manner as in Example 3, except that the final protein concentration of the adsorbed FFA tetanus vaccine was changed to 180 $\mu$g/ml. An adsorbed diphtheria toxoid and an adsorbed pertussis vaccine were individually prepared so that each of the toxoid concentration and the vaccine concentration became three times that of the working concentration. The adsorbed FFA tetanus vaccine, the adsorbed diphtheria toxoid and the adsorbed pertussis vaccine were mixed together to obtain an adsorbed DPT combined vaccine preparation. The obtained preparation was dispensed in glass vials each having a volume of 10 ml so that each vial contained 10 ml of the preparation, and then, the vials were sealed. The adsorbed DPT combined vaccine preparation was subjected to various tests in accordance with a provision entitled "adsorbed diphtheria-pertussis-tetanus combined vaccine" in the Notification No. 217 of the Japanese Ministry of Health and Welfare: "Seibutsugakuteki Seizai Kijun (Minimum Requirements for Biological Products)". As a result, the obtained preparation was verified as a qualified combined vaccine.

EXAMPLE 5

Production of an Adsorbed DT Combined Vaccine Preparation Using an FFA Tetanus Vaccine An adsorbed FFA tetanus vaccine was prepared in substantially the same manner as in Example 3, except that the final protein concentration of the adsorbed FFA tetanus vaccine was changed to 120 $\mu$g/ml. An adsorbed diphtheria toxoid was prepared so that the toxoid concentration became two times that of the working concentration. The adsorbed FFA tetanus vaccine and the diphtheria toxoid were mixed together to obtain an adsorbed DT combined vaccine preparation. The obtained preparation was dispensed in glass vials each having a volume of 1 ml so that each vial contained 0.6 ml of the preparation, and then, the vials were sealed. The obtained adsorbed DT combined vaccine preparation was subjected to various tests in accordance with a provision entitled "adsorbed diphtheria-tetanus combined vaccine" in the Notification No. 217 of the Japanese Ministry of Health and Welfare: "Seibutsugakuteki Seizai Kijun (Minimum Requirements for Biological Products)". As a result, the obtained preparation was verified as a qualified combined vaccine.

EXAMPLE 6

Production of a Dried FFA Tetanus Vaccine Preparation

An FFA tetanus vaccine preparation was prepared in substantially the same manner as in Example 2. The obtained FFA tetanus vaccine preparation was dispensed in glass vials each having a volume of 1 ml so that each vial contained 0.6 ml of the preparation, followed by freeze-drying to obtain a dried FFA tetanus vaccine preparation. Then, the vials were sealed. One of the vials was unsealed and the dried FFA tetanus vaccine preparation was dissolved by sterilized distilled water so as to obtain 0.6 ml of vaccine solution, and the obtained vaccine solution was subjected to various tests in accordance with a provision entitled "tetanus toxoid" in the Notification No. 217 of the Japanese Ministry of Health and Welfare "Seibutsugakuteki Seizai Kijun (Minimum Requirements for Biological Products)". As a result, the obtained preparation was verified as a qualified combined vaccine.

EXAMPLE 7

Production of a Sample FFA Tetanus Vaccine and Evaluation of the Immunopotency thereof The production of the vaccine using the extracellular toxin and the evaluation of the immunopotency of the produced vaccine were conducted in substantially the same manner as in Example 1, except that the conditions employed were changed as follows.

The time for culturing the seed culture of *C. tetani* at 35° C. was changed to 6 days. The preparation of the FFA from the solution of the whole tetanus toxin molecule (nicked form) obtained by gel filtration using Ultrogel AcA 34 column was conducted as follows. A DTT-Tris buffer (see Reference Example 8) was added to the above-mentioned solution of the whole tetanus toxin molecule in an amount of 1 ml per 2 mg of the solution of the whole tetanus toxin molecule, followed by mixing. Then, the reaction was performed at 25° C. for 60 minutes to reduce the disulfide bridge present in the toxin molecule. Subsequently, the resultant reaction mixture was treated with urea by addition of a solid urea in an amount such that the final urea concentration became 4 M. The reaction mixture was applied to PD10 column (manufactured and sold by Pharmacia Biotech, Sweden) equilibrated with the Buffer A (0.2 mM Tris-HCl containing 2 M urea solution and 1 mM DTT; pH 7.0) and the elution was carried out using the above-mentioned Buffer A to replace the DTT-Tris buffer in the reaction mixture with the Buffer A. The resultant eluate containing dissociated toxin was subjected to column chromatography using Mono Q column (manufactured and sold by Pharmacia Biotech, Sweden) equilibrated with Buffer A, wherein the elution was carried out using FPLC (manufactured and sold by Pharmacia Biotech, Sweden) and Buffer B (formed by adding NaCl to Buffer A, wherein the NaCl concentration is increased by a linear gradient of from 0 to 0.5 M). With respect to the obtained eluate, analysis was made in the same manner as in Example 1. As a result, it was found that, among the fractions of the eluate exhibiting a peak at 280 nm, the fraction obtained earliest was the FFA.

The stabilization of the FFA was conducted by incubating the FFA solution in a mixture of 0.067 M phosphate buffer (Na-K, pH 7.8) containing 0.2% (v/v) of formalin, and 0.025 M lysine at 35° C. for 2 weeks. The obtained stabilized FFA was used to prepare the FFA tetanus vaccine.

The evaluation of the immunopotency of the sample FFA tetanus vaccine was conducted by 4 sets of an experiment using mice in substantially the same manner as in item (5) of Example 1. Results are shown in Table 3. As can be clearly seen from Table 3, the immunopotency of the sample FFA tetanus vaccine had substantially the same level as that of the control vaccine comprising the whole tetanus toxin toxoid (i. e., a conventional tetanus toxoid).

TABLE 1

| Sample toxoid | Relative immunopotency | Fiducial limit (p = 0.95) |
|---|---|---|
| Purified whole toxin toxoid | 1.0 | |
| FFA | 0.970 | 0.636–1.478 |

Purified whole toxin toxoid: Vaccine comprising the whole tetanus toxin toxoid
FFA: Tetanus vaccine comprising the FFA

TABLE 2

| Amount of antigen administered by intradermal injection (μg) | | Antigen used for sensitization and the degree of intradermal reaction: Conventional toxoid | Purified whole tetanus toxoid | FFA |
|---|---|---|---|---|
| Conventional toxoid | 3.2 | +6 | +6 | +3 |
| | 1.0 | +6 | +5 | +2 |
| | 0.32 | +5 | +5 | +1 |
| Purified whole tetanus toxoid | 3.2 | +6 | +6 | +1 |
| | 1.0 | +4 | +5 | +1 |
| | 0.32 | +4 | +4 | *0 |
| FFA | 3.2 | +5 | +5 | +1 |
| | 1.0 | +3 | +3 | *0 |
| | 0.32 | +1 | +2 | *0 |
| Control | 0 | *0 | *0 | *0 |

Conventional toxoid: Commercially available tetanus toxoid
Purified whole tetanus toxoid: Vaccine comprising a whole tetanus toxin toxoid
FFA: Tetanus vaccine comprising the FFA The degree of intradermal reaction is shown, using an indication selected from seven indications (*0) to (+6), in accordance with the following criteria, based on the size (E) of the erythema wherein E is a value of formula:

$$\frac{\text{major diameter (mm)}}{\text{of the erythema}} \times \frac{\text{minor diameter (mm)}}{\text{of the erythema}}:$$

$$\begin{aligned} {}^{*}0&: (0 \leqq E < 1),\ +1: (1 \leqq E < 20),\ +2: (20 \leqq E < 40),\\ +3&: (40 \leqq E < 60),\ +4: (60 \leqq E < 80),\\ +5&: (80 \leqq E < 100),\ \text{and} +6: (100 \leqq E). \end{aligned}$$

TABLE 3

| Sample toxoid | Relative immunopotency | Fiducial limits (p = 0.95) |
|---|---|---|
| Purified whole toxin toxid | 1.0 | |
| FFA | 1.158 | 0.563–2.382 |

Purified whole toxin toxoid: Vaccine comprising the whole tetanus toxin toxoid
FFA: Tetanus vaccine comprising the FFA

INDUSTRIAL APPLICABILITY

According to the present invention, an FFA (tetanus toxin functional fragment antigen) for a tetanus vaccine is provided, which is advantageous not only in that it is extremely excellent with respect to the diminution of adverse side effects, as compared to the conventional tetanus toxoids but also in that it has an immunopotency which is substantially the same as that of a conventional tetanus toxoid.

By the use of the FFA of the present invention as an active component for a tetanus vaccine, there can be provided a tetanus vaccine which is not only extremely excellent with respect to the diminution of adverse side effects, as compared to a conventional tetanus toxoid vaccine, but also has an immunopotency which is substantially the same as that of a conventional tetanus toxoid vaccine.

Further, the above-mentioned tetanus vaccine can also be provided in the form of a combined vaccine comprising the tetanus vaccine and at least one vaccine other than the tetanus vaccine, such as a pertussis vaccine and a diphtheria vaccine.

What is claimed is:

1. A tetanus toxin functional fragment antigen which is stabilized with a fixative, wherein the tetanus toxin functional fragment antigen prior to stabilization with said fixative comprises at least one independent fragment which is obtained by a process comprising the steps of splitting at least one peptide bond selected from peptide bonds individually connecting mutually adjacent amino acid residues in a partial amino acid sequence between two cysteine residues participating in forming a disulfide bridge present in the N-terminal of the entire amino acid sequence of a whole tetanus toxin molecule, splitting said disulfide bridge, and splitting non-covalent bonds between groups of the tetanus toxin molecule;

said tetanus toxin functional fragment antigen prior to stabilization with said fixative having:

(a) a molecular weight of from 90000 to 110000 as measured by an SDS-polyacrylamide gel electrophoresis method; and (b) an isoelectric point of 7.25±0.5 as measured by an isoelectric focusing method, wherein each of said at least one independent fragment has an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

2. A combined vaccine comprising the tetanus toxin functional fragment antigen of claim 1 and at least one additional antigen selected from the group consisting of diphtheria toxoid and an antigen for pertussis vaccine, each in an effective immunogenic amount.

3. A method for producing a tetanus vaccine, which comprises stabilizing a tetanus toxin functional fragment antigen with a fixative, said tetanus toxin functional fragment antigen comprising at least one independent fragment which is obtained by a process comprising the steps of collecting and purifying an extracellular tetanus toxin from a culture filtrate of *Clostridium tetani* to obtain an extracellular tetanus toxin molecule, splitting a disulfide bridge of said extracellular tetanus toxin molecule, and splitting non-covalent bonds between groups on the extracellular tetanus toxin molecule; said tetanus toxin functional fragment antigen having:

(a) a molecular weight of from 90000 to 110000 as measured by an SDS-polyacrylamide gel electrophoresis method; and (b) an isoelectric point of 7.25±0.5 as measured by an isoelectric focusing method, wherein each of said at least one independent fragment has an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

4. A tetanus vaccine comprising, as an active component, the tetanus toxin functional fragment antigen of claim 1 in an effective immunogenic amount.

* * * * *

SEQUENCE LISTING

```
<160> NUMBER OF SEQ ID NOS: 17

<210> SEQ ID NO 1
<211> LENGTH: 1315
<212> TYPE: PRT
<213> ORGANISM: Clostridium tetani

<400> SEQUENCE: 1
```

-continued

```
Met Pro Ile Thr Ile Asn Asn Phe Arg Tyr Ser Asp Pro Val Asn Asn
  1               5                  10                  15

Asp Thr Ile Ile Met Met Glu Pro Pro Tyr Cys Lys Gly Leu Asp Ile
             20                  25                  30

Tyr Tyr Lys Ala Phe Lys Ile Thr Asp Arg Ile Trp Ile Val Pro Glu
         35                  40                  45

Arg Tyr Glu Phe Gly Thr Lys Pro Glu Asp Phe Asn Pro Pro Ser Ser
     50                  55                  60

Leu Ile Glu Gly Ala Ser Glu Tyr Tyr Asp Pro Asn Tyr Leu Arg Thr
 65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
```

-continued

```
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845
```

-continued

```
Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
        995                 1000                1005

Gly Glu Val Arg Gln Ile Thr Phe Arg Asp Leu Pro Asp Lys Phe Asn
   1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
               1045                1050                1055

Glu Ile Thr Gly Leu Gly Ala Ile Arg Glu Asp Asn Asn Ile Thr Leu
           1060                1065                1070

Lys Leu Asp Arg Cys Asn Asn Asn Asn Gln Tyr Val Ser Ile Asp Lys
       1075                1080                1085

Phe Arg Ile Phe Cys Lys Ala Leu Asn Pro Lys Glu Ile Glu Lys Leu
   1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
               1125                1130                1135

Ser Lys Asp Val Gln Leu Lys Asn Ile Thr Asp Tyr Met Tyr Leu Thr
           1140                1145                1150

Asn Ala Pro Ser Tyr Thr Asn Gly Lys Leu Asn Ile Tyr Tyr Arg Arg
       1155                1160                1165

Leu Tyr Asn Gly Leu Lys Phe Ile Ile Lys Arg Tyr Thr Pro Asn Asn
   1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
               1205                1210                1215

Ala Phe Asn Asn Leu Asp Arg Ile Leu Arg Val Gly Tyr Asn Ala Pro
           1220                1225                1230

Gly Ile Pro Leu Tyr Lys Lys Met Glu Ala Val Lys Leu Arg Asp Leu
       1235                1240                1245

Lys Thr Tyr Ser Val Gln Leu Lys Leu Tyr Asp Asp Lys Asn Ala Ser
   1250                1255                1260
```

-continued

```
Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
                1285                1290                1295

Lys Ile Leu Gly Cys Asp Trp Tyr Phe Val Pro Thr Asp Glu Gly Trp
            1300                1305                1310

Thr Asn Asp
        1315
```

<210> SEQ ID NO 2
<211> LENGTH: 29
<212> TYPE: PRT
<213> ORGANISM: Clostridium tetani

<400> SEQUENCE: 2

```
Lys Ile Ile Pro Pro Thr Asn Ile Arg Glu Asn Leu Tyr Asn Arg Thr
1               5                   10                  15

Ala Ser Leu Thr Asp Leu Gly Gly Glu Leu Cys Ile Lys
            20                  25
```

<210> SEQ ID NO 3
<211> LENGTH: 28
<212> TYPE: PRT
<213> ORGANISM: Clostridium tetani

<400> SEQUENCE: 3

```
Ile Ile Pro Pro Thr Asn Ile Arg Glu Asn Leu Tyr Asn Arg Thr Ala
1               5                   10                  15

Ser Leu Thr Asp Leu Gly Gly Glu Leu Cys Ile Lys
            20                  25
```

<210> SEQ ID NO 4
<211> LENGTH: 20
<212> TYPE: PRT
<213> ORGANISM: Clostridium tetani

<400> SEQUENCE: 4

```
Glu Asn Leu Tyr Asn Arg Thr Ala Ser Leu Thr Asp Leu Gly Gly Glu
1               5                   10                  15

Leu Cys Ile Lys
            20
```

<210> SEQ ID NO 5
<211> LENGTH: 19
<212> TYPE: PRT
<213> ORGANISM: Clostridium tetani

<400> SEQUENCE: 5

```
Asn Leu Tyr Asn Arg Thr Ala Ser Leu Thr Asp Leu Gly Gly Glu Leu
1               5                   10                  15

Cys Ile Lys
```

<210> SEQ ID NO 6
<211> LENGTH: 16
<212> TYPE: PRT
<213> ORGANISM: Clostridium tetani

<400> SEQUENCE: 6

```
Asn Arg Thr Ala Ser Leu Thr Asp Leu Gly Gly Glu Leu Cys Ile Lys
1               5                   10                  15
```

-continued

<210> SEQ ID NO 7
<211> LENGTH: 14
<212> TYPE: PRT
<213> ORGANISM: Clostridium tetani

<400> SEQUENCE: 7

Thr Ala Ser Leu Thr Asp Leu Gly Gly Glu Leu Cys Ile Lys
1 5 10

<210> SEQ ID NO 8
<211> LENGTH: 12
<212> TYPE: PRT
<213> ORGANISM: Clostridium tetani

<400> SEQUENCE: 8

Ser Leu Thr Asp Leu Gly Gly Glu Leu Cys Ile Lys
1 5 10

<210> SEQ ID NO 9
<211> LENGTH: 7
<212> TYPE: PRT
<213> ORGANISM: Clostridium tetani

<400> SEQUENCE: 9

Gly Gly Glu Leu Cys Ile Lys
1 5

<210> SEQ ID NO 10
<211> LENGTH: 875
<212> TYPE: PRT
<213> ORGANISM: Clostridium tetani
<220> FEATURE:
<223> OTHER INFORMATION: Amino Acids 441 to 1315 of SEQ ID NO: 1

<400> SEQUENCE: 10

Lys Ile Ile Pro Pro Thr Asn Ile Arg Glu Asn Leu Tyr Asn Arg Thr
1 5 10 15

Ala Ser Leu Thr Asp Leu Gly Gly Glu Leu Cys Ile Lys Ile Lys Asn
20 25 30

Glu Asp Leu Thr Phe Ile Ala Glu Lys Asn Ser Phe Ser Glu Glu Pro
35 40 45

Phe Gln Asp Glu Ile Val Ser Tyr Asn Thr Lys Asn Lys Pro Leu Asn
50 55 60

Phe Asn Tyr Ser Leu Asp Lys Ile Ile Val Asp Tyr Asn Leu Gln Ser
65 70 75 80

Lys Ile Thr Leu Pro Asn Asp Arg Thr Thr Pro Val Thr Lys Gly Ile
85 90 95

Pro Tyr Ala Pro Glu Tyr Lys Ser Asn Ala Ala Ser Thr Ile Glu Ile
100 105 110

His Asn Ile Asp Asp Asn Thr Ile Tyr Gln Tyr Leu Tyr Ala Gln Lys
115 120 125

Ser Pro Thr Thr Leu Gln Arg Ile Thr Met Thr Asn Ser Val Asp Asp
130 135 140

Ala Leu Ile Asn Ser Thr Lys Ile Tyr Ser Tyr Phe Pro Ser Val Ile
145 150 155 160

Ser Lys Val Asn Gln Gly Ala Gln Gly Ile Leu Phe Leu Gln Trp Val
165 170 175

Arg Asp Ile Ile Asp Asp Phe Thr Asn Glu Ser Ser Gln Lys Thr Thr
180 185 190

Ile Asp Lys Ile Ser Asp Val Ser Thr Ile Val Pro Tyr Ile Gly Pro

-continued

```
        195                 200                 205

Ala Leu Asn Ile Val Lys Gln Gly Tyr Glu Gly Asn Phe Ile Gly Ala
    210                 215                 220

Leu Glu Thr Thr Gly Val Val Leu Leu Leu Glu Tyr Ile Pro Glu Ile
225                 230                 235                 240

Thr Leu Pro Val Ile Ala Ala Leu Ser Ile Ala Glu Ser Ser Thr Gln
                245                 250                 255

Lys Glu Lys Ile Ile Lys Thr Ile Asp Asn Phe Leu Glu Lys Arg Tyr
            260                 265                 270

Glu Lys Trp Ile Glu Val Tyr Lys Leu Val Lys Ala Lys Trp Leu Gly
        275                 280                 285

Thr Val Asn Thr Gln Phe Gln Lys Arg Ser Tyr Gln Met Tyr Arg Ser
    290                 295                 300

Leu Glu Tyr Gln Val Asp Ala Ile Lys Lys Ile Ile Asp Tyr Glu Tyr
305                 310                 315                 320

Lys Ile Tyr Ser Gly Pro Asp Lys Glu Gln Ile Ala Asp Glu Ile Asn
                325                 330                 335

Asn Leu Lys Asn Lys Leu Glu Glu Lys Ala Asn Lys Ala Met Ile Asn
            340                 345                 350

Ile Asn Ile Phe Met Arg Glu Ser Ser Arg Ser Phe Leu Val Asn Gln
        355                 360                 365

Met Ile Asn Glu Ala Lys Lys Gln Leu Leu Glu Phe Asp Thr Gln Ser
    370                 375                 380

Lys Asn Ile Leu Met Gln Tyr Ile Lys Ala Asn Ser Lys Phe Ile Gly
385                 390                 395                 400

Ile Thr Glu Leu Lys Lys Leu Glu Ser Lys Ile Asn Lys Val Phe Ser
                405                 410                 415

Thr Pro Ile Pro Phe Ser Tyr Ser Lys Asn Leu Asp Cys Trp Val Asp
            420                 425                 430

Asn Glu Glu Asp Ile Asp Val Ile Leu Lys Lys Ser Thr Ile Leu Asn
        435                 440                 445

Leu Asp Ile Asn Asn Asp Ile Ile Ser Asp Ile Ser Gly Phe Asn Ser
    450                 455                 460

Ser Val Ile Thr Tyr Pro Asp Ala Gln Leu Val Pro Gly Ile Asn Gly
465                 470                 475                 480

Lys Ala Ile His Leu Val Asn Asn Glu Ser Ser Glu Val Ile Val His
                485                 490                 495

Lys Ala Met Asp Ile Glu Tyr Asn Asp Met Phe Asn Asn Phe Thr Val
            500                 505                 510

Ser Phe Trp Leu Arg Val Pro Lys Val Ser Ala Ser His Leu Glu Gln
        515                 520                 525

Tyr Gly Thr Asn Glu Tyr Ser Ile Ile Ser Ser Met Lys Lys His Ser
    530                 535                 540

Leu Ser Ile Gly Ser Gly Trp Ser Val Ser Leu Lys Gly Asn Asn Leu
545                 550                 555                 560

Ile Trp Thr Leu Lys Asp Ser Ala Gly Glu Val Arg Gln Ile Thr Phe
                565                 570                 575

Arg Asp Leu Pro Asp Lys Phe Asn Ala Tyr Leu Ala Asn Lys Trp Val
            580                 585                 590

Phe Ile Thr Ile Thr Asn Asp Arg Leu Ser Ser Ala Asn Leu Tyr Ile
        595                 600                 605

Asn Gly Val Leu Met Gly Ser Ala Glu Ile Thr Gly Leu Gly Ala Ile
    610                 615                 620
```

-continued

```
Arg Glu Asp Asn Asn Ile Thr Leu Lys Leu Asp Arg Cys Asn Asn Asn
625                 630                 635                 640

Asn Gln Tyr Val Ser Ile Asp Lys Phe Arg Ile Phe Cys Lys Ala Leu
                645                 650                 655

Asn Pro Lys Glu Ile Glu Lys Leu Tyr Thr Ser Tyr Leu Ser Ile Thr
            660                 665                 670

Phe Leu Arg Asp Phe Trp Gly Asn Pro Leu Arg Tyr Asp Thr Glu Tyr
        675                 680                 685

Tyr Leu Ile Pro Val Ala Ser Ser Ser Lys Asp Val Gln Leu Lys Asn
    690                 695                 700

Ile Thr Asp Tyr Met Tyr Leu Thr Asn Ala Pro Ser Tyr Thr Asn Gly
705                 710                 715                 720

Lys Leu Asn Ile Tyr Tyr Arg Arg Leu Tyr Asn Gly Leu Lys Phe Ile
                725                 730                 735

Ile Lys Arg Tyr Thr Pro Asn Asn Glu Ile Asp Ser Phe Val Lys Ser
            740                 745                 750

Gly Asp Phe Ile Lys Leu Tyr Val Ser Tyr Asn Asn Asn Glu His Ile
        755                 760                 765

Val Gly Tyr Pro Lys Asp Gly Asn Ala Phe Asn Asn Leu Asp Arg Ile
    770                 775                 780

Leu Arg Val Gly Tyr Asn Ala Pro Gly Ile Pro Leu Tyr Lys Lys Met
785                 790                 795                 800

Glu Ala Val Lys Leu Arg Asp Leu Lys Thr Tyr Ser Val Gln Leu Lys
                805                 810                 815

Leu Tyr Asp Asp Lys Asn Ala Ser Leu Gly Leu Val Gly Thr His Asn
            820                 825                 830

Gly Gln Ile Gly Asn Asp Pro Asn Arg Asp Ile Leu Ile Ala Ser Asn
        835                 840                 845

Trp Tyr Phe Asn His Leu Lys Asp Lys Ile Leu Gly Cys Asp Trp Tyr
    850                 855                 860

Phe Val Pro Thr Asp Glu Gly Trp Thr Asn Asp
865                 870                 875
```

<210> SEQ ID NO 11
<211> LENGTH: 874
<212> TYPE: PRT
<213> ORGANISM: Clostridium tetani
<220> FEATURE:
<223> OTHER INFORMATION: Amino Acids 442 to 1315 of SEQ ID NO: 1

<400> SEQUENCE: 11

```
Ile Ile Pro Pro Thr Asn Ile Arg Glu Asn Leu Tyr Asn Arg Thr Ala
  1               5                  10                  15

Ser Leu Thr Asp Leu Gly Gly Glu Leu Cys Ile Lys Ile Lys Asn Glu
             20                  25                  30

Asp Leu Thr Phe Ile Ala Glu Lys Asn Ser Phe Ser Glu Glu Pro Phe
         35                  40                  45

Gln Asp Glu Ile Val Ser Tyr Asn Thr Lys Asn Lys Pro Leu Asn Phe
     50                  55                  60

Asn Tyr Ser Leu Asp Lys Ile Ile Val Asp Tyr Asn Leu Gln Ser Lys
 65                  70                  75                  80

Ile Thr Leu Pro Asn Asp Arg Thr Thr Pro Val Thr Lys Gly Ile Pro
                 85                  90                  95

Tyr Ala Pro Glu Tyr Lys Ser Asn Ala Ala Ser Thr Ile Glu Ile His
            100                 105                 110
```

-continued

```
Asn Ile Asp Asp Asn Thr Ile Tyr Gln Tyr Leu Tyr Ala Gln Lys Ser
        115                 120                 125

Pro Thr Thr Leu Gln Arg Ile Thr Met Thr Asn Ser Val Asp Asp Ala
    130                 135                 140

Leu Ile Asn Ser Thr Lys Ile Tyr Ser Tyr Phe Pro Ser Val Ile Ser
145                 150                 155                 160

Lys Val Asn Gln Gly Ala Gln Gly Ile Leu Phe Leu Gln Trp Val Arg
                165                 170                 175

Asp Ile Ile Asp Asp Phe Thr Asn Glu Ser Ser Gln Lys Thr Thr Ile
            180                 185                 190

Asp Lys Ile Ser Asp Val Ser Thr Ile Val Pro Tyr Ile Gly Pro Ala
        195                 200                 205

Leu Asn Ile Val Lys Gln Gly Tyr Glu Gly Asn Phe Ile Gly Ala Leu
    210                 215                 220

Glu Thr Thr Gly Val Val Leu Leu Leu Glu Tyr Ile Pro Glu Ile Thr
225                 230                 235                 240

Leu Pro Val Ile Ala Ala Leu Ser Ile Ala Glu Ser Ser Thr Gln Lys
                245                 250                 255

Glu Lys Ile Ile Lys Thr Ile Asp Asn Phe Leu Glu Lys Arg Tyr Glu
            260                 265                 270

Lys Trp Ile Glu Val Tyr Lys Leu Val Lys Ala Lys Trp Leu Gly Thr
        275                 280                 285

Val Asn Thr Gln Phe Gln Lys Arg Ser Tyr Gln Met Tyr Arg Ser Leu
    290                 295                 300

Glu Tyr Gln Val Asp Ala Ile Lys Lys Ile Ile Asp Tyr Glu Tyr Lys
305                 310                 315                 320

Ile Tyr Ser Gly Pro Asp Lys Glu Gln Ile Ala Asp Glu Ile Asn Asn
                325                 330                 335

Leu Lys Asn Lys Leu Glu Glu Lys Ala Asn Lys Ala Met Ile Asn Ile
            340                 345                 350

Asn Ile Phe Met Arg Glu Ser Ser Arg Ser Phe Leu Val Asn Gln Met
        355                 360                 365

Ile Asn Glu Ala Lys Lys Gln Leu Leu Glu Phe Asp Thr Gln Ser Lys
    370                 375                 380

Asn Ile Leu Met Gln Tyr Ile Lys Ala Asn Ser Lys Phe Ile Gly Ile
385                 390                 395                 400

Thr Glu Leu Lys Lys Leu Glu Ser Lys Ile Asn Lys Val Phe Ser Thr
                405                 410                 415

Pro Ile Pro Phe Ser Tyr Ser Lys Asn Leu Asp Cys Trp Val Asp Asn
            420                 425                 430

Glu Glu Asp Ile Asp Val Ile Leu Lys Lys Ser Thr Ile Leu Asn Leu
        435                 440                 445

Asp Ile Asn Asn Asp Ile Ile Ser Asp Ile Ser Gly Phe Asn Ser Ser
    450                 455                 460

Val Ile Thr Tyr Pro Asp Ala Gln Leu Val Pro Gly Ile Asn Gly Lys
465                 470                 475                 480

Ala Ile His Leu Val Asn Asn Glu Ser Ser Glu Val Ile Val His Lys
                485                 490                 495

Ala Met Asp Ile Glu Tyr Asn Asp Met Phe Asn Asn Phe Thr Val Ser
            500                 505                 510

Phe Trp Leu Arg Val Pro Lys Val Ser Ala Ser His Leu Glu Gln Tyr
        515                 520                 525
```

-continued

Gly Thr Asn Glu Tyr Ser Ile Ile Ser Ser Met Lys Lys His Ser Leu
530 535 540

Ser Ile Gly Ser Gly Trp Ser Val Ser Leu Lys Gly Asn Asn Leu Ile
545 550 555 560

Trp Thr Leu Lys Asp Ser Ala Gly Glu Val Arg Gln Ile Thr Phe Arg
565 570 575

Asp Leu Pro Asp Lys Phe Asn Ala Tyr Leu Ala Asn Lys Trp Val Phe
580 585 590

Ile Thr Ile Thr Asn Asp Arg Leu Ser Ser Ala Asn Leu Tyr Ile Asn
595 600 605

Gly Val Leu Met Gly Ser Ala Glu Ile Thr Gly Leu Gly Ala Ile Arg
610 615 620

Glu Asp Asn Asn Ile Thr Leu Lys Leu Asp Arg Cys Asn Asn Asn Asn
625 630 635 640

Gln Tyr Val Ser Ile Asp Lys Phe Arg Ile Phe Cys Lys Ala Leu Asn
645 650 655

Pro Lys Glu Ile Glu Lys Leu Tyr Thr Ser Tyr Leu Ser Ile Thr Phe
660 665 670

Leu Arg Asp Phe Trp Gly Asn Pro Leu Arg Tyr Asp Thr Glu Tyr Tyr
675 680 685

Leu Ile Pro Val Ala Ser Ser Ser Lys Asp Val Gln Leu Lys Asn Ile
690 695 700

Thr Asp Tyr Met Tyr Leu Thr Asn Ala Pro Ser Tyr Thr Asn Gly Lys
705 710 715 720

Leu Asn Ile Tyr Tyr Arg Arg Leu Tyr Asn Gly Leu Lys Phe Ile Ile
725 730 735

Lys Arg Tyr Thr Pro Asn Asn Glu Ile Asp Ser Phe Val Lys Ser Gly
740 745 750

Asp Phe Ile Lys Leu Tyr Val Ser Tyr Asn Asn Asn Glu His Ile Val
755 760 765

Gly Tyr Pro Lys Asp Gly Asn Ala Phe Asn Asn Leu Asp Arg Ile Leu
770 775 780

Arg Val Gly Tyr Asn Ala Pro Gly Ile Pro Leu Tyr Lys Lys Met Glu
785 790 795 800

Ala Val Lys Leu Arg Asp Leu Lys Thr Tyr Ser Val Gln Leu Lys Leu
805 810 815

Tyr Asp Asp Lys Asn Ala Ser Leu Gly Leu Val Gly Thr His Asn Gly
820 825 830

Gln Ile Gly Asn Asp Pro Asn Arg Asp Ile Leu Ile Ala Ser Asn Trp
835 840 845

Tyr Phe Asn His Leu Lys Asp Lys Ile Leu Gly Cys Asp Trp Tyr Phe
850 855 860

Val Pro Thr Asp Glu Gly Trp Thr Asn Asp
865 870

<210> SEQ ID NO 12
<211> LENGTH: 866
<212> TYPE: PRT
<213> ORGANISM: Clostridium tetani
<220> FEATURE:
<223> OTHER INFORMATION: Amino Acids 450 to 1315 of SEQ ID NO: 1

<400> SEQUENCE: 12

Glu Asn Leu Tyr Asn Arg Thr Ala Ser Leu Thr Asp Leu Gly Gly Glu
1 5 10 15

-continued

```
Leu Cys Ile Lys Ile Lys Asn Glu Asp Leu Thr Phe Ile Ala Glu Lys
            20                  25                  30

Asn Ser Phe Ser Glu Glu Pro Phe Gln Asp Glu Ile Val Ser Tyr Asn
        35                  40                  45

Thr Lys Asn Lys Pro Leu Asn Phe Asn Tyr Ser Leu Asp Lys Ile Ile
    50                  55                  60

Val Asp Tyr Asn Leu Gln Ser Lys Ile Thr Leu Pro Asn Asp Arg Thr
65                  70                  75                  80

Thr Pro Val Thr Lys Gly Ile Pro Tyr Ala Pro Glu Tyr Lys Ser Asn
                85                  90                  95

Ala Ala Ser Thr Ile Glu Ile His Asn Ile Asp Asp Asn Thr Ile Tyr
            100                 105                 110

Gln Tyr Leu Tyr Ala Gln Lys Ser Pro Thr Thr Leu Gln Arg Ile Thr
        115                 120                 125

Met Thr Asn Ser Val Asp Asp Ala Leu Ile Asn Ser Thr Lys Ile Tyr
    130                 135                 140

Ser Tyr Phe Pro Ser Val Ile Ser Lys Val Asn Gln Gly Ala Gln Gly
145                 150                 155                 160

Ile Leu Phe Leu Gln Trp Val Arg Asp Ile Ile Asp Asp Phe Thr Asn
                165                 170                 175

Glu Ser Ser Gln Lys Thr Thr Ile Asp Lys Ile Ser Asp Val Ser Thr
            180                 185                 190

Ile Val Pro Tyr Ile Gly Pro Ala Leu Asn Ile Val Lys Gln Gly Tyr
        195                 200                 205

Glu Gly Asn Phe Ile Gly Ala Leu Glu Thr Thr Gly Val Val Leu Leu
    210                 215                 220

Leu Glu Tyr Ile Pro Glu Ile Thr Leu Pro Val Ile Ala Ala Leu Ser
225                 230                 235                 240

Ile Ala Glu Ser Ser Thr Gln Lys Glu Lys Ile Ile Lys Thr Ile Asp
                245                 250                 255

Asn Phe Leu Glu Lys Arg Tyr Glu Lys Trp Ile Glu Val Tyr Lys Leu
            260                 265                 270

Val Lys Ala Lys Trp Leu Gly Thr Val Asn Thr Gln Phe Gln Lys Arg
        275                 280                 285

Ser Tyr Gln Met Tyr Arg Ser Leu Glu Tyr Gln Val Asp Ala Ile Lys
    290                 295                 300

Lys Ile Ile Asp Tyr Glu Tyr Lys Ile Tyr Ser Gly Pro Asp Lys Glu
305                 310                 315                 320

Gln Ile Ala Asp Glu Ile Asn Asn Leu Lys Asn Lys Leu Glu Glu Lys
                325                 330                 335

Ala Asn Lys Ala Met Ile Asn Ile Asn Ile Phe Met Arg Glu Ser Ser
            340                 345                 350

Arg Ser Phe Leu Val Asn Gln Met Ile Asn Glu Ala Lys Lys Gln Leu
        355                 360                 365

Leu Glu Phe Asp Thr Gln Ser Lys Asn Ile Leu Met Gln Tyr Ile Lys
    370                 375                 380

Ala Asn Ser Lys Phe Ile Gly Ile Thr Glu Leu Lys Lys Leu Glu Ser
385                 390                 395                 400

Lys Ile Asn Lys Val Phe Ser Thr Pro Ile Pro Phe Ser Tyr Ser Lys
                405                 410                 415

Asn Leu Asp Cys Trp Val Asp Asn Glu Glu Asp Ile Asp Val Ile Leu
            420                 425                 430

Lys Lys Ser Thr Ile Leu Asn Leu Asp Ile Asn Asn Asp Ile Ile Ser
```

-continued

```
        435                 440                 445

Asp Ile Ser Gly Phe Asn Ser Ser Val Ile Thr Tyr Pro Asp Ala Gln
    450                 455                 460

Leu Val Pro Gly Ile Asn Gly Lys Ala Ile His Leu Val Asn Asn Glu
465                 470                 475                 480

Ser Ser Glu Val Ile Val His Lys Ala Met Asp Ile Glu Tyr Asn Asp
                485                 490                 495

Met Phe Asn Asn Phe Thr Val Ser Phe Trp Leu Arg Val Pro Lys Val
            500                 505                 510

Ser Ala Ser His Leu Glu Gln Tyr Gly Thr Asn Glu Tyr Ser Ile Ile
        515                 520                 525

Ser Ser Met Lys Lys His Ser Leu Ser Ile Gly Ser Gly Trp Ser Val
    530                 535                 540

Ser Leu Lys Gly Asn Asn Leu Ile Trp Thr Leu Lys Asp Ser Ala Gly
545                 550                 555                 560

Glu Val Arg Gln Ile Thr Phe Arg Asp Leu Pro Asp Lys Phe Asn Ala
                565                 570                 575

Tyr Leu Ala Asn Lys Trp Val Phe Ile Thr Ile Thr Asn Asp Arg Leu
            580                 585                 590

Ser Ser Ala Asn Leu Tyr Ile Asn Gly Val Leu Met Gly Ser Ala Glu
        595                 600                 605

Ile Thr Gly Leu Gly Ala Ile Arg Glu Asp Asn Asn Ile Thr Leu Lys
    610                 615                 620

Leu Asp Arg Cys Asn Asn Asn Asn Gln Tyr Val Ser Ile Asp Lys Phe
625                 630                 635                 640

Arg Ile Phe Cys Lys Ala Leu Asn Pro Lys Glu Ile Glu Lys Leu Tyr
                645                 650                 655

Thr Ser Tyr Leu Ser Ile Thr Phe Leu Arg Asp Phe Trp Gly Asn Pro
            660                 665                 670

Leu Arg Tyr Asp Thr Glu Tyr Tyr Leu Ile Pro Val Ala Ser Ser Ser
        675                 680                 685

Lys Asp Val Gln Leu Lys Asn Ile Thr Asp Tyr Met Tyr Leu Thr Asn
    690                 695                 700

Ala Pro Ser Tyr Thr Asn Gly Lys Leu Asn Ile Tyr Tyr Arg Arg Leu
705                 710                 715                 720

Tyr Asn Gly Leu Lys Phe Ile Ile Lys Arg Tyr Thr Pro Asn Asn Glu
                725                 730                 735

Ile Asp Ser Phe Val Lys Ser Gly Asp Phe Ile Lys Leu Tyr Val Ser
            740                 745                 750

Tyr Asn Asn Asn Glu His Ile Val Gly Tyr Pro Lys Asp Gly Asn Ala
        755                 760                 765

Phe Asn Asn Leu Asp Arg Ile Leu Arg Val Gly Tyr Asn Ala Pro Gly
    770                 775                 780

Ile Pro Leu Tyr Lys Lys Met Glu Ala Val Lys Leu Arg Asp Leu Lys
785                 790                 795                 800

Thr Tyr Ser Val Gln Leu Lys Leu Tyr Asp Asp Lys Asn Ala Ser Leu
                805                 810                 815

Gly Leu Val Gly Thr His Asn Gly Gln Ile Gly Asn Asp Pro Asn Arg
            820                 825                 830

Asp Ile Leu Ile Ala Ser Asn Trp Tyr Phe Asn His Leu Lys Asp Lys
        835                 840                 845

Ile Leu Gly Cys Asp Trp Tyr Phe Val Pro Thr Asp Glu Gly Trp Thr
    850                 855                 860
```

Asn Asp
865

<210> SEQ ID NO 13
<211> LENGTH: 865
<212> TYPE: PRT
<213> ORGANISM: Clostridium tetani
<220> FEATURE:
<223> OTHER INFORMATION: Amino Acids 451 to 1315 of SEQ ID NO: 1

<400> SEQUENCE: 13

```
Asn Leu Tyr Asn Arg Thr Ala Ser Leu Thr Asp Leu Gly Gly Glu Leu
  1               5                  10                  15

Cys Ile Lys Ile Lys Asn Glu Asp Leu Thr Phe Ile Ala Glu Lys Asn
             20                  25                  30

Ser Phe Ser Glu Glu Pro Phe Gln Asp Glu Ile Val Ser Tyr Asn Thr
         35                  40                  45

Lys Asn Lys Pro Leu Asn Phe Asn Tyr Ser Leu Asp Lys Ile Ile Val
     50                  55                  60

Asp Tyr Asn Leu Gln Ser Lys Ile Thr Leu Pro Asn Asp Arg Thr Thr
 65                  70                  75                  80

Pro Val Thr Lys Gly Ile Pro Tyr Ala Pro Glu Tyr Lys Ser Asn Ala
                 85                  90                  95

Ala Ser Thr Ile Glu Ile His Asn Ile Asp Asp Asn Thr Ile Tyr Gln
            100                 105                 110

Tyr Leu Tyr Ala Gln Lys Ser Pro Thr Thr Leu Gln Arg Ile Thr Met
        115                 120                 125

Thr Asn Ser Val Asp Asp Ala Leu Ile Asn Ser Thr Lys Ile Tyr Ser
    130                 135                 140

Tyr Phe Pro Ser Val Ile Ser Lys Val Asn Gln Gly Ala Gln Gly Ile
145                 150                 155                 160

Leu Phe Leu Gln Trp Val Arg Asp Ile Ile Asp Asp Phe Thr Asn Glu
                165                 170                 175

Ser Ser Gln Lys Thr Thr Ile Asp Lys Ile Ser Asp Val Ser Thr Ile
            180                 185                 190

Val Pro Tyr Ile Gly Pro Ala Leu Asn Ile Val Lys Gln Gly Tyr Glu
        195                 200                 205

Gly Asn Phe Ile Gly Ala Leu Glu Thr Thr Gly Val Val Leu Leu Leu
    210                 215                 220

Glu Tyr Ile Pro Glu Ile Thr Leu Pro Val Ile Ala Ala Leu Ser Ile
225                 230                 235                 240

Ala Glu Ser Ser Thr Gln Lys Glu Lys Ile Ile Lys Thr Ile Asp Asn
                245                 250                 255

Phe Leu Glu Lys Arg Tyr Glu Lys Trp Ile Glu Val Tyr Lys Leu Val
            260                 265                 270

Lys Ala Lys Trp Leu Gly Thr Val Asn Thr Gln Phe Gln Lys Arg Ser
        275                 280                 285

Tyr Gln Met Tyr Arg Ser Leu Glu Tyr Gln Val Asp Ala Ile Lys Lys
    290                 295                 300

Ile Ile Asp Tyr Glu Tyr Lys Ile Tyr Ser Gly Pro Asp Lys Glu Gln
305                 310                 315                 320

Ile Ala Asp Glu Ile Asn Asn Leu Lys Asn Lys Leu Glu Glu Lys Ala
                325                 330                 335

Asn Lys Ala Met Ile Asn Ile Asn Ile Phe Met Arg Glu Ser Ser Arg
            340                 345                 350
```

-continued

```
Ser Phe Leu Val Asn Gln Met Ile Asn Glu Ala Lys Lys Gln Leu Leu
        355                 360                 365

Glu Phe Asp Thr Gln Ser Lys Asn Ile Leu Met Gln Tyr Ile Lys Ala
    370                 375                 380

Asn Ser Lys Phe Ile Gly Ile Thr Glu Leu Lys Lys Leu Glu Ser Lys
385                 390                 395                 400

Ile Asn Lys Val Phe Ser Thr Pro Ile Pro Phe Ser Tyr Ser Lys Asn
                405                 410                 415

Leu Asp Cys Trp Val Asp Asn Glu Glu Asp Ile Asp Val Ile Leu Lys
            420                 425                 430

Lys Ser Thr Ile Leu Asn Leu Asp Ile Asn Asn Asp Ile Ile Ser Asp
        435                 440                 445

Ile Ser Gly Phe Asn Ser Ser Val Ile Thr Tyr Pro Asp Ala Gln Leu
    450                 455                 460

Val Pro Gly Ile Asn Gly Lys Ala Ile His Leu Val Asn Asn Glu Ser
465                 470                 475                 480

Ser Glu Val Ile Val His Lys Ala Met Asp Ile Glu Tyr Asn Asp Met
                485                 490                 495

Phe Asn Asn Phe Thr Val Ser Phe Trp Leu Arg Val Pro Lys Val Ser
            500                 505                 510

Ala Ser His Leu Glu Gln Tyr Gly Thr Asn Glu Tyr Ser Ile Ile Ser
        515                 520                 525

Ser Met Lys Lys His Ser Leu Ser Ile Gly Ser Gly Trp Ser Val Ser
    530                 535                 540

Leu Lys Gly Asn Asn Leu Ile Trp Thr Leu Lys Asp Ser Ala Gly Glu
545                 550                 555                 560

Val Arg Gln Ile Thr Phe Arg Asp Leu Pro Asp Lys Phe Asn Ala Tyr
                565                 570                 575

Leu Ala Asn Lys Trp Val Phe Ile Thr Ile Thr Asn Asp Arg Leu Ser
            580                 585                 590

Ser Ala Asn Leu Tyr Ile Asn Gly Val Leu Met Gly Ser Ala Glu Ile
        595                 600                 605

Thr Gly Leu Gly Ala Ile Arg Glu Asp Asn Asn Ile Thr Leu Lys Leu
    610                 615                 620

Asp Arg Cys Asn Asn Asn Asn Gln Tyr Val Ser Ile Asp Lys Phe Arg
625                 630                 635                 640

Ile Phe Cys Lys Ala Leu Asn Pro Lys Glu Ile Glu Lys Leu Tyr Thr
                645                 650                 655

Ser Tyr Leu Ser Ile Thr Phe Leu Arg Asp Phe Trp Gly Asn Pro Leu
            660                 665                 670

Arg Tyr Asp Thr Glu Tyr Tyr Leu Ile Pro Val Ala Ser Ser Ser Lys
        675                 680                 685

Asp Val Gln Leu Lys Asn Ile Thr Asp Tyr Met Tyr Leu Thr Asn Ala
    690                 695                 700

Pro Ser Tyr Thr Asn Gly Lys Leu Asn Ile Tyr Tyr Arg Arg Leu Tyr
705                 710                 715                 720

Asn Gly Leu Lys Phe Ile Ile Lys Arg Tyr Thr Pro Asn Asn Glu Ile
                725                 730                 735

Asp Ser Phe Val Lys Ser Gly Asp Phe Ile Lys Leu Tyr Val Ser Tyr
            740                 745                 750

Asn Asn Asn Glu His Ile Val Gly Tyr Pro Lys Asp Gly Asn Ala Phe
        755                 760                 765
```

-continued

```
Asn Asn Leu Asp Arg Ile Leu Arg Val Gly Tyr Asn Ala Pro Gly Ile
    770                 775                 780

Pro Leu Tyr Lys Lys Met Glu Ala Val Lys Leu Arg Asp Leu Lys Thr
785                 790                 795                 800

Tyr Ser Val Gln Leu Lys Leu Tyr Asp Asp Lys Asn Ala Ser Leu Gly
                805                 810                 815

Leu Val Gly Thr His Asn Gly Gln Ile Gly Asn Asp Pro Asn Arg Asp
            820                 825                 830

Ile Leu Ile Ala Ser Asn Trp Tyr Phe Asn His Leu Lys Asp Lys Ile
        835                 840                 845

Leu Gly Cys Asp Trp Tyr Phe Val Pro Thr Asp Glu Gly Trp Thr Asn
    850                 855                 860

Asp
865


<210> SEQ ID NO 14
<211> LENGTH: 862
<212> TYPE: PRT
<213> ORGANISM: Clostridium tetani
<220> FEATURE:
<223> OTHER INFORMATION: Amino Acids 454 to 1315 of SEQ ID NO: 1

<400> SEQUENCE: 14

Asn Arg Thr Ala Ser Leu Thr Asp Leu Gly Gly Glu Leu Cys Ile Lys
  1               5                  10                  15

Ile Lys Asn Glu Asp Leu Thr Phe Ile Ala Glu Lys Asn Ser Phe Ser
             20                  25                  30

Glu Glu Pro Phe Gln Asp Glu Ile Val Ser Tyr Asn Thr Lys Asn Lys
         35                  40                  45

Pro Leu Asn Phe Asn Tyr Ser Leu Asp Lys Ile Ile Val Asp Tyr Asn
     50                  55                  60

Leu Gln Ser Lys Ile Thr Leu Pro Asn Asp Arg Thr Thr Pro Val Thr
 65                  70                  75                  80

Lys Gly Ile Pro Tyr Ala Pro Glu Tyr Lys Ser Asn Ala Ala Ser Thr
                 85                  90                  95

Ile Glu Ile His Asn Ile Asp Asp Asn Thr Ile Tyr Gln Tyr Leu Tyr
            100                 105                 110

Ala Gln Lys Ser Pro Thr Thr Leu Gln Arg Ile Thr Met Thr Asn Ser
        115                 120                 125

Val Asp Asp Ala Leu Ile Asn Ser Thr Lys Ile Tyr Ser Tyr Phe Pro
    130                 135                 140

Ser Val Ile Ser Lys Val Asn Gln Gly Ala Gln Gly Ile Leu Phe Leu
145                 150                 155                 160

Gln Trp Val Arg Asp Ile Ile Asp Asp Phe Thr Asn Glu Ser Ser Gln
                165                 170                 175

Lys Thr Thr Ile Asp Lys Ile Ser Asp Val Ser Thr Ile Val Pro Tyr
            180                 185                 190

Ile Gly Pro Ala Leu Asn Ile Val Lys Gln Gly Tyr Glu Gly Asn Phe
        195                 200                 205

Ile Gly Ala Leu Glu Thr Thr Gly Val Val Leu Leu Leu Glu Tyr Ile
    210                 215                 220

Pro Glu Ile Thr Leu Pro Val Ile Ala Ala Leu Ser Ile Ala Glu Ser
225                 230                 235                 240

Ser Thr Gln Lys Glu Lys Ile Ile Lys Thr Ile Asp Asn Phe Leu Glu
                245                 250                 255
```

-continued

```
Lys Arg Tyr Glu Lys Trp Ile Glu Val Tyr Lys Leu Val Lys Ala Lys
            260                 265                 270

Trp Leu Gly Thr Val Asn Thr Gln Phe Gln Lys Arg Ser Tyr Gln Met
        275                 280                 285

Tyr Arg Ser Leu Glu Tyr Gln Val Asp Ala Ile Lys Lys Ile Ile Asp
    290                 295                 300

Tyr Glu Tyr Lys Ile Tyr Ser Gly Pro Asp Lys Glu Gln Ile Ala Asp
305                 310                 315                 320

Glu Ile Asn Asn Leu Lys Asn Lys Leu Glu Glu Lys Ala Asn Lys Ala
                325                 330                 335

Met Ile Asn Ile Asn Ile Phe Met Arg Glu Ser Ser Arg Ser Phe Leu
            340                 345                 350

Val Asn Gln Met Ile Asn Glu Ala Lys Lys Gln Leu Leu Glu Phe Asp
        355                 360                 365

Thr Gln Ser Lys Asn Ile Leu Met Gln Tyr Ile Lys Ala Asn Ser Lys
    370                 375                 380

Phe Ile Gly Ile Thr Glu Leu Lys Lys Leu Glu Ser Lys Ile Asn Lys
385                 390                 395                 400

Val Phe Ser Thr Pro Ile Pro Phe Ser Tyr Ser Lys Asn Leu Asp Cys
                405                 410                 415

Trp Val Asp Asn Glu Glu Asp Ile Asp Val Ile Leu Lys Lys Ser Thr
            420                 425                 430

Ile Leu Asn Leu Asp Ile Asn Asn Asp Ile Ile Ser Asp Ile Ser Gly
        435                 440                 445

Phe Asn Ser Ser Val Ile Thr Tyr Pro Asp Ala Gln Leu Val Pro Gly
    450                 455                 460

Ile Asn Gly Lys Ala Ile His Leu Val Asn Asn Glu Ser Ser Glu Val
465                 470                 475                 480

Ile Val His Lys Ala Met Asp Ile Glu Tyr Asn Asp Met Phe Asn Asn
                485                 490                 495

Phe Thr Val Ser Phe Trp Leu Arg Val Pro Lys Val Ser Ala Ser His
            500                 505                 510

Leu Glu Gln Tyr Gly Thr Asn Glu Tyr Ser Ile Ile Ser Ser Met Lys
        515                 520                 525

Lys His Ser Leu Ser Ile Gly Ser Gly Trp Ser Val Ser Leu Lys Gly
    530                 535                 540

Asn Asn Leu Ile Trp Thr Leu Lys Asp Ser Ala Gly Glu Val Arg Gln
545                 550                 555                 560

Ile Thr Phe Arg Asp Leu Pro Asp Lys Phe Asn Ala Tyr Leu Ala Asn
                565                 570                 575

Lys Trp Val Phe Ile Thr Ile Thr Asn Asp Arg Leu Ser Ser Ala Asn
            580                 585                 590

Leu Tyr Ile Asn Gly Val Leu Met Gly Ser Ala Glu Ile Thr Gly Leu
        595                 600                 605

Gly Ala Ile Arg Glu Asp Asn Asn Ile Thr Leu Lys Leu Asp Arg Cys
    610                 615                 620

Asn Asn Asn Asn Gln Tyr Val Ser Ile Asp Lys Phe Arg Ile Phe Cys
625                 630                 635                 640

Lys Ala Leu Asn Pro Lys Glu Ile Glu Lys Leu Tyr Thr Ser Tyr Leu
                645                 650                 655

Ser Ile Thr Phe Leu Arg Asp Phe Trp Gly Asn Pro Leu Arg Tyr Asp
            660                 665                 670

Thr Glu Tyr Tyr Leu Ile Pro Val Ala Ser Ser Ser Lys Asp Val Gln
```

-continued

```
        675                 680                 685

Leu Lys Asn Ile Thr Asp Tyr Met Tyr Leu Thr Asn Ala Pro Ser Tyr
    690                 695                 700

Thr Asn Gly Lys Leu Asn Ile Tyr Tyr Arg Arg Leu Tyr Asn Gly Leu
705                 710                 715                 720

Lys Phe Ile Ile Lys Arg Tyr Thr Pro Asn Asn Glu Ile Asp Ser Phe
                725                 730                 735

Val Lys Ser Gly Asp Phe Ile Lys Leu Tyr Val Ser Tyr Asn Asn Asn
            740                 745                 750

Glu His Ile Val Gly Tyr Pro Lys Asp Gly Asn Ala Phe Asn Asn Leu
        755                 760                 765

Asp Arg Ile Leu Arg Val Gly Tyr Asn Ala Pro Gly Ile Pro Leu Tyr
    770                 775                 780

Lys Lys Met Glu Ala Val Lys Leu Arg Asp Leu Lys Thr Tyr Ser Val
785                 790                 795                 800

Gln Leu Lys Leu Tyr Asp Asp Lys Asn Ala Ser Leu Gly Leu Val Gly
                805                 810                 815

Thr His Asn Gly Gln Ile Gly Asn Asp Pro Asn Arg Asp Ile Leu Ile
            820                 825                 830

Ala Ser Asn Trp Tyr Phe Asn His Leu Lys Asp Lys Ile Leu Gly Cys
        835                 840                 845

Asp Trp Tyr Phe Val Pro Thr Asp Glu Gly Trp Thr Asn Asp
    850                 855                 860


<210> SEQ ID NO 15
<211> LENGTH: 860
<212> TYPE: PRT
<213> ORGANISM: Clostridium tetani
<220> FEATURE:
<223> OTHER INFORMATION: Amino Acids 456 to 1315 of SEQ ID NO: 1

<400> SEQUENCE: 15

Thr Ala Ser Leu Thr Asp Leu Gly Gly Glu Leu Cys Ile Lys Ile Lys
  1               5                  10                  15

Asn Glu Asp Leu Thr Phe Ile Ala Glu Lys Asn Ser Phe Ser Glu Glu
             20                  25                  30

Pro Phe Gln Asp Glu Ile Val Ser Tyr Asn Thr Lys Asn Lys Pro Leu
        35                  40                  45

Asn Phe Asn Tyr Ser Leu Asp Lys Ile Ile Val Asp Tyr Asn Leu Gln
     50                  55                  60

Ser Lys Ile Thr Leu Pro Asn Asp Arg Thr Thr Pro Val Thr Lys Gly
 65                  70                  75                  80

Ile Pro Tyr Ala Pro Glu Tyr Lys Ser Asn Ala Ala Ser Thr Ile Glu
                 85                  90                  95

Ile His Asn Ile Asp Asp Asn Thr Ile Tyr Gln Tyr Leu Tyr Ala Gln
            100                 105                 110

Lys Ser Pro Thr Thr Leu Gln Arg Ile Thr Met Thr Asn Ser Val Asp
        115                 120                 125

Asp Ala Leu Ile Asn Ser Thr Lys Ile Tyr Ser Tyr Phe Pro Ser Val
    130                 135                 140

Ile Ser Lys Val Asn Gln Gly Ala Gln Gly Ile Leu Phe Leu Gln Trp
145                 150                 155                 160

Val Arg Asp Ile Ile Asp Asp Phe Thr Asn Glu Ser Ser Gln Lys Thr
                165                 170                 175

Thr Ile Asp Lys Ile Ser Asp Val Ser Thr Ile Val Pro Tyr Ile Gly
```

-continued

```
            180                 185                 190

Pro Ala Leu Asn Ile Val Lys Gln Gly Tyr Glu Gly Asn Phe Ile Gly
        195                 200                 205

Ala Leu Glu Thr Thr Gly Val Val Leu Leu Leu Glu Tyr Ile Pro Glu
    210                 215                 220

Ile Thr Leu Pro Val Ile Ala Ala Leu Ser Ile Ala Glu Ser Ser Thr
225                 230                 235                 240

Gln Lys Glu Lys Ile Ile Lys Thr Ile Asp Asn Phe Leu Glu Lys Arg
                245                 250                 255

Tyr Glu Lys Trp Ile Glu Val Tyr Lys Leu Val Lys Ala Lys Trp Leu
            260                 265                 270

Gly Thr Val Asn Thr Gln Phe Gln Lys Arg Ser Tyr Gln Met Tyr Arg
        275                 280                 285

Ser Leu Glu Tyr Gln Val Asp Ala Ile Lys Lys Ile Ile Asp Tyr Glu
    290                 295                 300

Tyr Lys Ile Tyr Ser Gly Pro Asp Lys Glu Gln Ile Ala Asp Glu Ile
305                 310                 315                 320

Asn Asn Leu Lys Asn Lys Leu Glu Glu Lys Ala Asn Lys Ala Met Ile
                325                 330                 335

Asn Ile Asn Ile Phe Met Arg Glu Ser Ser Arg Ser Phe Leu Val Asn
            340                 345                 350

Gln Met Ile Asn Glu Ala Lys Lys Gln Leu Leu Glu Phe Asp Thr Gln
        355                 360                 365

Ser Lys Asn Ile Leu Met Gln Tyr Ile Lys Ala Asn Ser Lys Phe Ile
    370                 375                 380

Gly Ile Thr Glu Leu Lys Lys Leu Glu Ser Lys Ile Asn Lys Val Phe
385                 390                 395                 400

Ser Thr Pro Ile Pro Phe Ser Tyr Ser Lys Asn Leu Asp Cys Trp Val
                405                 410                 415

Asp Asn Glu Glu Asp Ile Asp Val Ile Leu Lys Lys Ser Thr Ile Leu
            420                 425                 430

Asn Leu Asp Ile Asn Asn Asp Ile Ile Ser Asp Ile Ser Gly Phe Asn
        435                 440                 445

Ser Ser Val Ile Thr Tyr Pro Asp Ala Gln Leu Val Pro Gly Ile Asn
    450                 455                 460

Gly Lys Ala Ile His Leu Val Asn Asn Glu Ser Ser Glu Val Ile Val
465                 470                 475                 480

His Lys Ala Met Asp Ile Glu Tyr Asn Asp Met Phe Asn Asn Phe Thr
                485                 490                 495

Val Ser Phe Trp Leu Arg Val Pro Lys Val Ser Ala Ser His Leu Glu
            500                 505                 510

Gln Tyr Gly Thr Asn Glu Tyr Ser Ile Ile Ser Ser Met Lys Lys His
        515                 520                 525

Ser Leu Ser Ile Gly Ser Gly Trp Ser Val Ser Leu Lys Gly Asn Asn
    530                 535                 540

Leu Ile Trp Thr Leu Lys Asp Ser Ala Gly Glu Val Arg Gln Ile Thr
545                 550                 555                 560

Phe Arg Asp Leu Pro Asp Lys Phe Asn Ala Tyr Leu Ala Asn Lys Trp
                565                 570                 575

Val Phe Ile Thr Ile Thr Asn Asp Arg Leu Ser Ser Ala Asn Leu Tyr
            580                 585                 590

Ile Asn Gly Val Leu Met Gly Ser Ala Glu Ile Thr Gly Leu Gly Ala
        595                 600                 605
```

-continued

Ile Arg Glu Asp Asn Asn Ile Thr Leu Lys Leu Asp Arg Cys Asn Asn
    610                 615                 620

Asn Asn Gln Tyr Val Ser Ile Asp Lys Phe Arg Ile Phe Cys Lys Ala
625                 630                 635                 640

Leu Asn Pro Lys Glu Ile Glu Lys Leu Tyr Thr Ser Tyr Leu Ser Ile
                645                 650                 655

Thr Phe Leu Arg Asp Phe Trp Gly Asn Pro Leu Arg Tyr Asp Thr Glu
            660                 665                 670

Tyr Tyr Leu Ile Pro Val Ala Ser Ser Ser Lys Asp Val Gln Leu Lys
        675                 680                 685

Asn Ile Thr Asp Tyr Met Tyr Leu Thr Asn Ala Pro Ser Tyr Thr Asn
    690                 695                 700

Gly Lys Leu Asn Ile Tyr Tyr Arg Arg Leu Tyr Asn Gly Leu Lys Phe
705                 710                 715                 720

Ile Ile Lys Arg Tyr Thr Pro Asn Asn Glu Ile Asp Ser Phe Val Lys
                725                 730                 735

Ser Gly Asp Phe Ile Lys Leu Tyr Val Ser Tyr Asn Asn Asn Glu His
            740                 745                 750

Ile Val Gly Tyr Pro Lys Asp Gly Asn Ala Phe Asn Asn Leu Asp Arg
        755                 760                 765

Ile Leu Arg Val Gly Tyr Asn Ala Pro Gly Ile Pro Leu Tyr Lys Lys
    770                 775                 780

Met Glu Ala Val Lys Leu Arg Asp Leu Lys Thr Tyr Ser Val Gln Leu
785                 790                 795                 800

Lys Leu Tyr Asp Asp Lys Asn Ala Ser Leu Gly Leu Val Gly Thr His
                805                 810                 815

Asn Gly Gln Ile Gly Asn Asp Pro Asn Arg Asp Ile Leu Ile Ala Ser
            820                 825                 830

Asn Trp Tyr Phe Asn His Leu Lys Asp Lys Ile Leu Gly Cys Asp Trp
        835                 840                 845

Tyr Phe Val Pro Thr Asp Glu Gly Trp Thr Asn Asp
    850                 855                 860

<210> SEQ ID NO 16
<211> LENGTH: 858
<212> TYPE: PRT
<213> ORGANISM: Clostridium tetani
<220> FEATURE:
<223> OTHER INFORMATION: Amino Acids 458 to 1315 of SEQ ID NO: 1

<400> SEQUENCE: 16

Ser Leu Thr Asp Leu Gly Gly Glu Leu Cys Ile Lys Ile Lys Asn Glu
  1               5                  10                  15

Asp Leu Thr Phe Ile Ala Glu Lys Asn Ser Phe Ser Glu Glu Pro Phe
             20                  25                  30

Gln Asp Glu Ile Val Ser Tyr Asn Thr Lys Asn Lys Pro Leu Asn Phe
         35                  40                  45

Asn Tyr Ser Leu Asp Lys Ile Ile Val Asp Tyr Asn Leu Gln Ser Lys
     50                  55                  60

Ile Thr Leu Pro Asn Asp Arg Thr Thr Pro Val Thr Lys Gly Ile Pro
 65                  70                  75                  80

Tyr Ala Pro Glu Tyr Lys Ser Asn Ala Ala Ser Thr Ile Glu Ile His
                 85                  90                  95

Asn Ile Asp Asp Asn Thr Ile Tyr Gln Tyr Leu Tyr Ala Gln Lys Ser
            100                 105                 110

-continued

```
Pro Thr Thr Leu Gln Arg Ile Thr Met Thr Asn Ser Val Asp Asp Ala
        115                 120                 125

Leu Ile Asn Ser Thr Lys Ile Tyr Ser Tyr Phe Pro Ser Val Ile Ser
    130                 135                 140

Lys Val Asn Gln Gly Ala Gln Gly Ile Leu Phe Leu Gln Trp Val Arg
145                 150                 155                 160

Asp Ile Ile Asp Asp Phe Thr Asn Glu Ser Ser Gln Lys Thr Thr Ile
                165                 170                 175

Asp Lys Ile Ser Asp Val Ser Thr Ile Val Pro Tyr Ile Gly Pro Ala
            180                 185                 190

Leu Asn Ile Val Lys Gln Gly Tyr Glu Gly Asn Phe Ile Gly Ala Leu
        195                 200                 205

Glu Thr Thr Gly Val Val Leu Leu Leu Glu Tyr Ile Pro Glu Ile Thr
    210                 215                 220

Leu Pro Val Ile Ala Ala Leu Ser Ile Ala Glu Ser Ser Thr Gln Lys
225                 230                 235                 240

Glu Lys Ile Ile Lys Thr Ile Asp Asn Phe Leu Glu Lys Arg Tyr Glu
                245                 250                 255

Lys Trp Ile Glu Val Tyr Lys Leu Val Lys Ala Lys Trp Leu Gly Thr
            260                 265                 270

Val Asn Thr Gln Phe Gln Lys Arg Ser Tyr Gln Met Tyr Arg Ser Leu
        275                 280                 285

Glu Tyr Gln Val Asp Ala Ile Lys Lys Ile Ile Asp Tyr Glu Tyr Lys
    290                 295                 300

Ile Tyr Ser Gly Pro Asp Lys Glu Gln Ile Ala Asp Glu Ile Asn Asn
305                 310                 315                 320

Leu Lys Asn Lys Leu Glu Glu Lys Ala Asn Lys Ala Met Ile Asn Ile
                325                 330                 335

Asn Ile Phe Met Arg Glu Ser Ser Arg Ser Phe Leu Val Asn Gln Met
            340                 345                 350

Ile Asn Glu Ala Lys Lys Gln Leu Leu Glu Phe Asp Thr Gln Ser Lys
        355                 360                 365

Asn Ile Leu Met Gln Tyr Ile Lys Ala Asn Ser Lys Phe Ile Gly Ile
    370                 375                 380

Thr Glu Leu Lys Lys Leu Glu Ser Lys Ile Asn Lys Val Phe Ser Thr
385                 390                 395                 400

Pro Ile Pro Phe Ser Tyr Ser Lys Asn Leu Asp Cys Trp Val Asp Asn
                405                 410                 415

Glu Glu Asp Ile Asp Val Ile Leu Lys Lys Ser Thr Ile Leu Asn Leu
            420                 425                 430

Asp Ile Asn Asn Asp Ile Ile Ser Asp Ile Ser Gly Phe Asn Ser Ser
        435                 440                 445

Val Ile Thr Tyr Pro Asp Ala Gln Leu Val Pro Gly Ile Asn Gly Lys
    450                 455                 460

Ala Ile His Leu Val Asn Asn Glu Ser Ser Glu Val Ile Val His Lys
465                 470                 475                 480

Ala Met Asp Ile Glu Tyr Asn Asp Met Phe Asn Asn Phe Thr Val Ser
                485                 490                 495

Phe Trp Leu Arg Val Pro Lys Val Ser Ala Ser His Leu Glu Gln Tyr
            500                 505                 510

Gly Thr Asn Glu Tyr Ser Ile Ile Ser Ser Met Lys Lys His Ser Leu
        515                 520                 525
```

-continued

```
Ser Ile Gly Ser Gly Trp Ser Val Ser Leu Lys Gly Asn Asn Leu Ile
    530                 535                 540

Trp Thr Leu Lys Asp Ser Ala Gly Glu Val Arg Gln Ile Thr Phe Arg
545                 550                 555                 560

Asp Leu Pro Asp Lys Phe Asn Ala Tyr Leu Ala Asn Lys Trp Val Phe
                565                 570                 575

Ile Thr Ile Thr Asn Asp Arg Leu Ser Ser Ala Asn Leu Tyr Ile Asn
            580                 585                 590

Gly Val Leu Met Gly Ser Ala Glu Ile Thr Gly Leu Gly Ala Ile Arg
        595                 600                 605

Glu Asp Asn Asn Ile Thr Leu Lys Leu Asp Arg Cys Asn Asn Asn Asn
    610                 615                 620

Gln Tyr Val Ser Ile Asp Lys Phe Arg Ile Phe Cys Lys Ala Leu Asn
625                 630                 635                 640

Pro Lys Glu Ile Glu Lys Leu Tyr Thr Ser Tyr Leu Ser Ile Thr Phe
                645                 650                 655

Leu Arg Asp Phe Trp Gly Asn Pro Leu Arg Tyr Asp Thr Glu Tyr Tyr
            660                 665                 670

Leu Ile Pro Val Ala Ser Ser Ser Lys Asp Val Gln Leu Lys Asn Ile
        675                 680                 685

Thr Asp Tyr Met Tyr Leu Thr Asn Ala Pro Ser Tyr Thr Asn Gly Lys
    690                 695                 700

Leu Asn Ile Tyr Tyr Arg Arg Leu Tyr Asn Gly Leu Lys Phe Ile Ile
705                 710                 715                 720

Lys Arg Tyr Thr Pro Asn Asn Glu Ile Asp Ser Phe Val Lys Ser Gly
                725                 730                 735

Asp Phe Ile Lys Leu Tyr Val Ser Tyr Asn Asn Asn Glu His Ile Val
            740                 745                 750

Gly Tyr Pro Lys Asp Gly Asn Ala Phe Asn Asn Leu Asp Arg Ile Leu
        755                 760                 765

Arg Val Gly Tyr Asn Ala Pro Gly Ile Pro Leu Tyr Lys Lys Met Glu
    770                 775                 780

Ala Val Lys Leu Arg Asp Leu Lys Thr Tyr Ser Val Gln Leu Lys Leu
785                 790                 795                 800

Tyr Asp Asp Lys Asn Ala Ser Leu Gly Leu Val Gly Thr His Asn Gly
                805                 810                 815

Gln Ile Gly Asn Asp Pro Asn Arg Asp Ile Leu Ile Ala Ser Asn Trp
            820                 825                 830

Tyr Phe Asn His Leu Lys Asp Lys Ile Leu Gly Cys Asp Trp Tyr Phe
        835                 840                 845

Val Pro Thr Asp Glu Gly Trp Thr Asn Asp
    850                 855


<210> SEQ ID NO 17
<211> LENGTH: 853
<212> TYPE: PRT
<213> ORGANISM: Clostridium tetani
<220> FEATURE:
<223> OTHER INFORMATION: Amino Acids 463 to 1315 of SEQ ID NO: 1

<400> SEQUENCE: 17

Gly Gly Glu Leu Cys Ile Lys Ile Lys Asn Glu Asp Leu Thr Phe Ile
  1               5                  10                  15

Ala Glu Lys Asn Ser Phe Ser Glu Glu Pro Phe Gln Asp Glu Ile Val
             20                  25                  30
```

-continued

```
Ser Tyr Asn Thr Lys Asn Lys Pro Leu Asn Phe Asn Tyr Ser Leu Asp
         35                  40                  45

Lys Ile Ile Val Asp Tyr Asn Leu Gln Ser Lys Ile Thr Leu Pro Asn
     50                  55                  60

Asp Arg Thr Thr Pro Val Thr Lys Gly Ile Pro Tyr Ala Pro Glu Tyr
 65                  70                  75                  80

Lys Ser Asn Ala Ala Ser Thr Ile Glu Ile His Asn Ile Asp Asp Asn
                 85                  90                  95

Thr Ile Tyr Gln Tyr Leu Tyr Ala Gln Lys Ser Pro Thr Thr Leu Gln
            100                 105                 110

Arg Ile Thr Met Thr Asn Ser Val Asp Asp Ala Leu Ile Asn Ser Thr
        115                 120                 125

Lys Ile Tyr Ser Tyr Phe Pro Ser Val Ile Ser Lys Val Asn Gln Gly
    130                 135                 140

Ala Gln Gly Ile Leu Phe Leu Gln Trp Val Arg Asp Ile Ile Asp Asp
145                 150                 155                 160

Phe Thr Asn Glu Ser Ser Gln Lys Thr Thr Ile Asp Lys Ile Ser Asp
                165                 170                 175

Val Ser Thr Ile Val Pro Tyr Ile Gly Pro Ala Leu Asn Ile Val Lys
            180                 185                 190

Gln Gly Tyr Glu Gly Asn Phe Ile Gly Ala Leu Glu Thr Thr Gly Val
        195                 200                 205

Val Leu Leu Leu Glu Tyr Ile Pro Glu Ile Thr Leu Pro Val Ile Ala
    210                 215                 220

Ala Leu Ser Ile Ala Glu Ser Ser Thr Gln Lys Glu Lys Ile Ile Lys
225                 230                 235                 240

Thr Ile Asp Asn Phe Leu Glu Lys Arg Tyr Glu Lys Trp Ile Glu Val
                245                 250                 255

Tyr Lys Leu Val Lys Ala Lys Trp Leu Gly Thr Val Asn Thr Gln Phe
            260                 265                 270

Gln Lys Arg Ser Tyr Gln Met Tyr Arg Ser Leu Glu Tyr Gln Val Asp
        275                 280                 285

Ala Ile Lys Lys Ile Ile Asp Tyr Glu Tyr Lys Ile Tyr Ser Gly Pro
    290                 295                 300

Asp Lys Glu Gln Ile Ala Asp Glu Ile Asn Asn Leu Lys Asn Lys Leu
305                 310                 315                 320

Glu Glu Lys Ala Asn Lys Ala Met Ile Asn Ile Asn Ile Phe Met Arg
                325                 330                 335

Glu Ser Ser Arg Ser Phe Leu Val Asn Gln Met Ile Asn Glu Ala Lys
            340                 345                 350

Lys Gln Leu Leu Glu Phe Asp Thr Gln Ser Lys Asn Ile Leu Met Gln
        355                 360                 365

Tyr Ile Lys Ala Asn Ser Lys Phe Ile Gly Ile Thr Glu Leu Lys Lys
    370                 375                 380

Leu Glu Ser Lys Ile Asn Lys Val Phe Ser Thr Pro Ile Pro Phe Ser
385                 390                 395                 400

Tyr Ser Lys Asn Leu Asp Cys Trp Val Asp Asn Glu Glu Asp Ile Asp
                405                 410                 415

Val Ile Leu Lys Lys Ser Thr Ile Leu Asn Leu Asp Ile Asn Asn Asp
            420                 425                 430

Ile Ile Ser Asp Ile Ser Gly Phe Asn Ser Ser Val Ile Thr Tyr Pro
        435                 440                 445

Asp Ala Gln Leu Val Pro Gly Ile Asn Gly Lys Ala Ile His Leu Val
```

-continued

```
    450                 455                 460

Asn Asn Glu Ser Ser Glu Val Ile Val His Lys Ala Met Asp Ile Glu
465                 470                 475                 480

Tyr Asn Asp Met Phe Asn Asn Phe Thr Val Ser Phe Trp Leu Arg Val
                485                 490                 495

Pro Lys Val Ser Ala Ser His Leu Glu Gln Tyr Gly Thr Asn Glu Tyr
            500                 505                 510

Ser Ile Ile Ser Ser Met Lys Lys His Ser Leu Ser Ile Gly Ser Gly
        515                 520                 525

Trp Ser Val Ser Leu Lys Gly Asn Asn Leu Ile Trp Thr Leu Lys Asp
    530                 535                 540

Ser Ala Gly Glu Val Arg Gln Ile Thr Phe Arg Asp Leu Pro Asp Lys
545                 550                 555                 560

Phe Asn Ala Tyr Leu Ala Asn Lys Trp Val Phe Ile Thr Ile Thr Asn
                565                 570                 575

Asp Arg Leu Ser Ser Ala Asn Leu Tyr Ile Asn Gly Val Leu Met Gly
            580                 585                 590

Ser Ala Glu Ile Thr Gly Leu Gly Ala Ile Arg Glu Asp Asn Asn Ile
        595                 600                 605

Thr Leu Lys Leu Asp Arg Cys Asn Asn Asn Asn Gln Tyr Val Ser Ile
    610                 615                 620

Asp Lys Phe Arg Ile Phe Cys Lys Ala Leu Asn Pro Lys Glu Ile Glu
625                 630                 635                 640

Lys Leu Tyr Thr Ser Tyr Leu Ser Ile Thr Phe Leu Arg Asp Phe Trp
                645                 650                 655

Gly Asn Pro Leu Arg Tyr Asp Thr Glu Tyr Tyr Leu Ile Pro Val Ala
            660                 665                 670

Ser Ser Ser Lys Asp Val Gln Leu Lys Asn Ile Thr Asp Tyr Met Tyr
        675                 680                 685

Leu Thr Asn Ala Pro Ser Tyr Thr Asn Gly Lys Leu Asn Ile Tyr Tyr
    690                 695                 700

Arg Arg Leu Tyr Asn Gly Leu Lys Phe Ile Ile Lys Arg Tyr Thr Pro
705                 710                 715                 720

Asn Asn Glu Ile Asp Ser Phe Val Lys Ser Gly Asp Phe Ile Lys Leu
                725                 730                 735

Tyr Val Ser Tyr Asn Asn Asn Glu His Ile Val Gly Tyr Pro Lys Asp
            740                 745                 750

Gly Asn Ala Phe Asn Asn Leu Asp Arg Ile Leu Arg Val Gly Tyr Asn
        755                 760                 765

Ala Pro Gly Ile Pro Leu Tyr Lys Lys Met Glu Ala Val Lys Leu Arg
    770                 775                 780

Asp Leu Lys Thr Tyr Ser Val Gln Leu Lys Leu Tyr Asp Asp Lys Asn
785                 790                 795                 800

Ala Ser Leu Gly Leu Val Gly Thr His Asn Gly Gln Ile Gly Asn Asp
                805                 810                 815

Pro Asn Arg Asp Ile Leu Ile Ala Ser Asn Trp Tyr Phe Asn His Leu
            820                 825                 830

Lys Asp Lys Ile Leu Gly Cys Asp Trp Tyr Phe Val Pro Thr Asp Glu
        835                 840                 845

Gly Trp Thr Asn Asp
    850
```